United States Patent
Erdem et al.

(10) Patent No.: US 10,053,321 B2
(45) Date of Patent: Aug. 21, 2018

(54) SPOOL OF A THREE-DIMENSIONAL SUBSTRATE

(71) Applicant: The Procter & Gamble Company, Cincinnati, OH (US)

(72) Inventors: Gueltekin Erdem, Schwalbach Am Taunus (DE); Bruno Ehrnsperger, Bad Soden (DE); Holger Beruda, Schwalbach Am Taunus (DE); Nadezhda Kurbatova, Schwalbach Am Taunus (DE); Joseph Lam, Mason, OH (US); Walter Pieter Hendrik Laurentius van der Klugt, Mechernich Satzvey (DE); Sudhanshu Gupta, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 300 days.

(21) Appl. No.: 15/071,516

(22) Filed: Mar. 16, 2016

(65) Prior Publication Data
US 2016/0280490 A1  Sep. 29, 2016

Related U.S. Application Data

(60) Provisional application No. 62/138,426, filed on Mar. 26, 2015.

(30) Foreign Application Priority Data

Mar. 26, 2015  (EP) .................................... 15161010

(51) Int. Cl.
*B65H 18/28* (2006.01)
*B65H 18/08* (2006.01)
(Continued)

(52) U.S. Cl.
CPC ....... *B65H 18/28* (2013.01); *A61F 13/15747* (2013.01); *A61F 13/15764* (2013.01);
(Continued)

(58) Field of Classification Search
CPC .... B65H 18/28; B65H 18/08; B65H 2801/57; B65H 2301/412845; A61F 13/15747; A61F 13/15764; A61F 13/51104
See application file for complete search history.

(56) References Cited

U.S. PATENT DOCUMENTS 2,717,037 A    9/1955  Goodwillie et al.
3,025,015 A *  3/1962  Mix ...................... B65H 75/02
                                                    242/613.2
(Continued)

FOREIGN PATENT DOCUMENTS

GB    2350375      11/2000
JP    S63300058    12/1988
(Continued)

OTHER PUBLICATIONS

EP Search Report, EP Application No. EP15161010.
(Continued)

*Primary Examiner* — William E Dondero
(74) *Attorney, Agent, or Firm* — Christian M. Best

(57) ABSTRACT

A spool comprises a three-dimensional substrate and a core. The three-dimensional substrate comprises a plurality of projections extending outwardly from a plane of the substrate. The spool comprises a first plurality of spirally wound portions and a first plurality of helically wound portions. The substrate is spirally wound around the core to form each spirally wound portion of the first plurality of spirally wound portions. The spirally wound portions of the first plurality of spirally wound portions are located next to each other along a longitudinal axis of the core between a first transversal side
(Continued)

edge of the core and a second transversal side edge of the core. The substrate is helically wound around the core along the longitudinal axis of the core to form each helically wound portion. Each helically wound portion extends between two adjacent spirally wound portions of the first plurality of spirally wound portions.

19 Claims, 13 Drawing Sheets

(51) Int. Cl.
*A61F 13/511* (2006.01)
*A61F 13/15* (2006.01)

(52) U.S. Cl.
CPC ........ *A61F 13/51104* (2013.01); *B65H 18/08* (2013.01); *B65H 2301/412845* (2013.01); *B65H 2801/57* (2013.01)

(56) References Cited

U.S. PATENT DOCUMENTS

| | | |
|---|---|---|
| 3,549,099 A | 12/1970 | Hofbauer et al. |
| 4,024,696 A | 5/1977 | Townsend |
| 4,267,985 A | 5/1981 | Rogers |
| 4,634,070 A | 1/1987 | Looper |
| 6,007,016 A | 12/1999 | Helton |
| 6,138,934 A | 10/2000 | Helton |
| 6,209,814 B1 | 4/2001 | Helton |
| 6,533,213 B2 | 3/2003 | Durrance et al. |
| 8,157,197 B2 | 4/2012 | Jelinek et al. |
| 9,932,186 B2 | 4/2018 | Erdem et al. |
| 2003/0047632 A1 | 3/2003 | Duncan |
| 2003/0122009 A1 | 7/2003 | Abba et al. |
| 2013/0135728 A1 | 5/2013 | Hirata et al. |
| 2016/0280503 A1 | 9/2016 | Erdem et al. |

FOREIGN PATENT DOCUMENTS

| | | |
|---|---|---|
| JP | H11208954 | 8/1999 |
| JP | 2005287725 | 10/2005 |

OTHER PUBLICATIONS

All Office Actions for U.S. Appl. No. 15/071,532.
All Office Actions for U.S. Appl. No. 15/071,553.
International Search Report and Written Opinion, PCT/US2016/022266, dated May 19, 2016.

\* cited by examiner

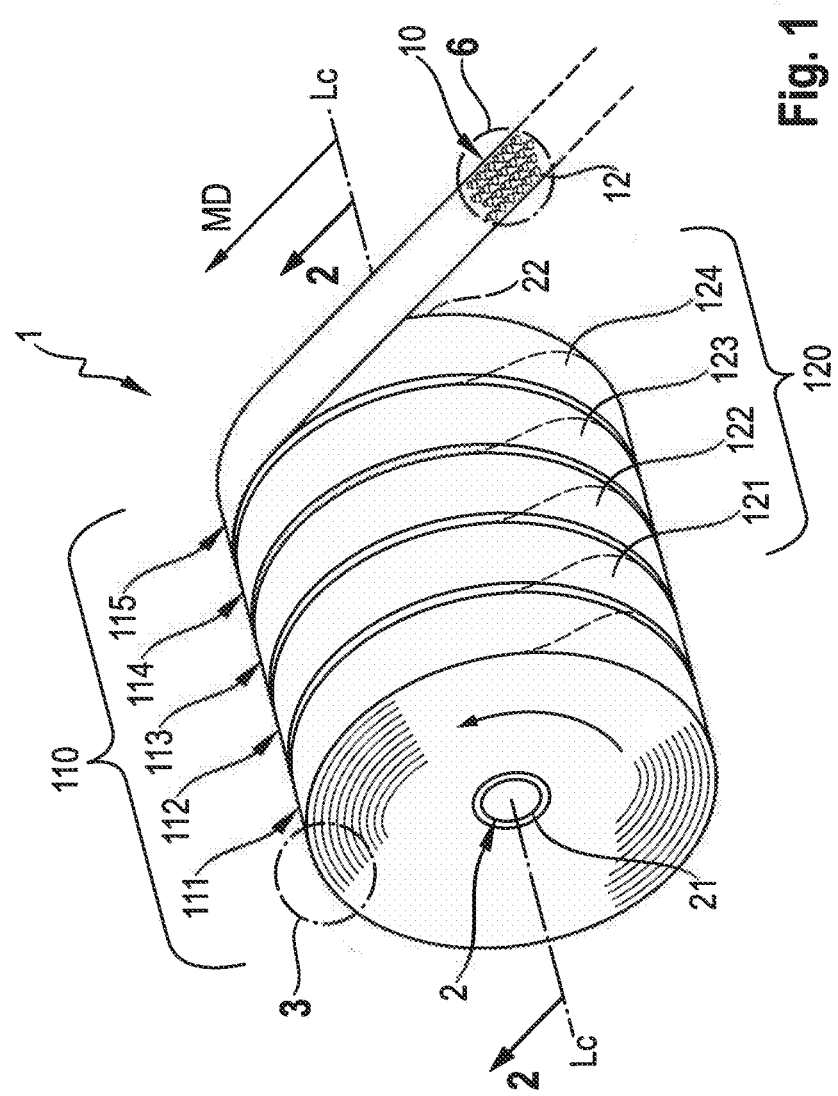

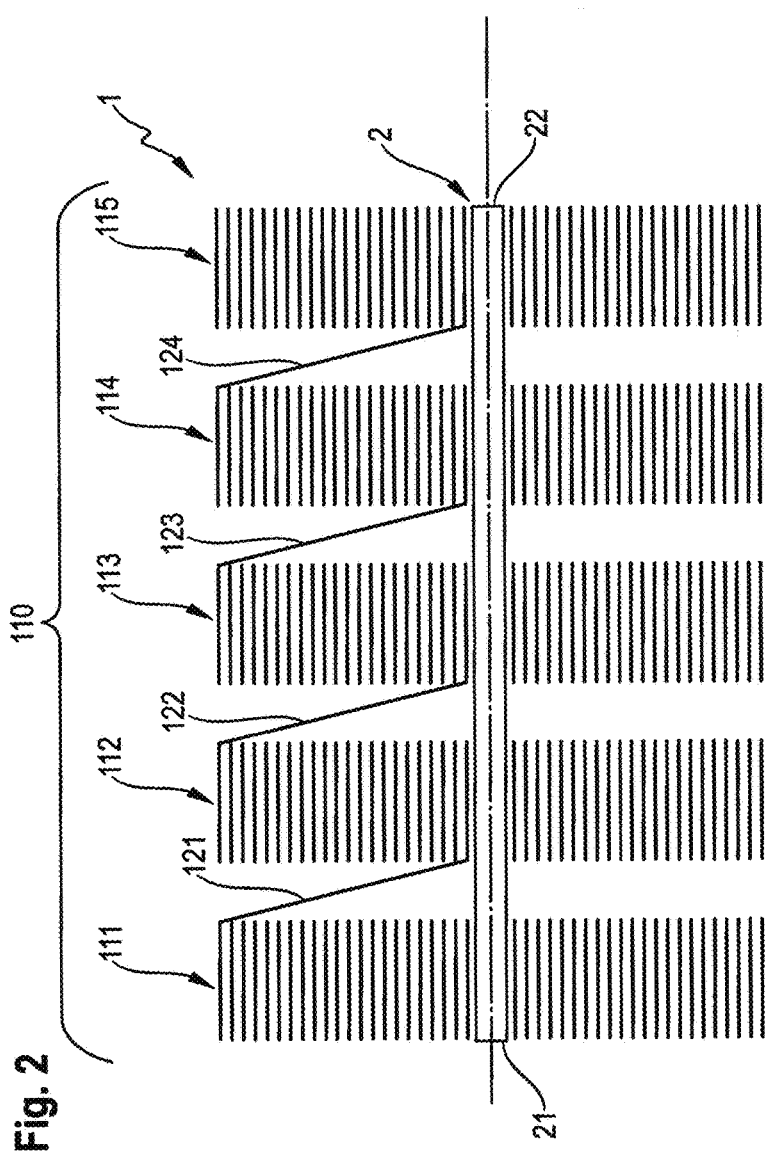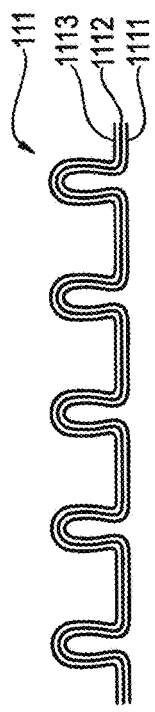

SPOOL OF A THREE-DIMENSIONAL SUBSTRATE

CROSS REFERENCE TO RELATED APPLICATION

This application claims the benefit, under 35 U.S.C. § 119, to EP Patent Application No. 15161010.2, filed on Mar. 26, 2015, and to U.S. Provisional Patent Application Ser. No. 62/138,426, filed on Mar. 26, 2015, both of which are fully incorporated by reference herein.

FIELD OF THE INVENTION

The present invention provides a spool comprising a three-dimensional substrate. The three-dimensional substrate has a plane and comprises a plurality of projections extending outwardly from the plane of the three-dimensional substrate. A method for making such spool is also provided.

BACKGROUND OF THE INVENTION

Absorbent articles for personal hygiene, such as disposable diapers for infants, training pants for toddlers, adult incontinence undergarments, and/or sanitary napkins are designed to absorb and contain bodily exudates, in particular large quantities of urine, runny BM, and/or menses (together the "fluids"). These absorbent articles may comprise several layers providing different functions, for example, a topsheet, a backsheet, and an absorbent core disposed between the topsheet and the backsheet, among other layers, if desired.

Topsheets comprising a three-dimensional substrate have been provided in order to further reduce skin/fluid contact and to enhance comfort.

The three-dimensional substrate has a plane and comprises a plurality of projections extending outwardly from the plane of the three-dimensional substrate. The projections are responsible in part for providing the above benefits in the absorbent article due to their three-dimensional characteristics.

Typical liquid permeable substrates are stored and provided via a conventional planar roll during the converting manufacturing process to make the absorbent article. Generally, the substrate is spirally wound around a core to form a plurality of overlaying layers in the planar roll. However, due to the pressure exerted on the overlaying layers in the planar roll, the projections of a three-dimensional substrate may not be preserved, resulting in fully or partially collapsed projections.

Also, when a conventional planar roll, comprising the three-dimensional substrate, is unwound to make the absorbent article, the run time is relatively low. This is due to the lofty nature of the projections of the three-dimensional substrate.

Hence, there is a need to provide a system that will preserve the three-dimensional characteristics of the plurality of projections of the three-dimensional substrate during the winding and storing of the three-dimensional substrate, and also enabling relatively high run times at absorbent article manufacturing lines.

SUMMARY OF THE INVENTION

A spool is provided and comprises a three-dimensional substrate and a core. The three-dimensional substrate has a plane and comprises a plurality of projections extending outwardly from the plane of the three-dimensional substrate. The three-dimensional substrate is made from the group consisting of a nonwoven web, a film and combinations thereof. The core has a longitudinal axis and a length along the longitudinal axis. The core comprises first and second transversal side edges.

The spool comprises a first plurality of spirally wound portions and a first plurality of helically wound portions. The three-dimensional substrate is spirally wound around the core to form each spirally wound portion of the first plurality of spirally wound portions. The spirally wound portions of the first plurality of spirally wound portions are located next to each other along the longitudinal axis of the core between the first transversal side edge of the core and the second transversal side edge of the core. The three-dimensional substrate is helically wound around the core along the longitudinal axis of the core to form each helically wound portion of the first plurality of helically wound portions. Each helically wound portion of the first plurality of helically wound portions extends between two adjacent spirally wound portions of the first plurality of spirally wound portions.

The three-dimensional substrate in each spirally wound portion of the first plurality of spirally wound portions is repeatedly and spirally wound around the core to form a plurality of layers overlaying each other. In each spirally wound portion, a majority of the projections of the three-dimensional substrate in at least some of the layers are at least partially nested with a majority of the projections of the three-dimensional substrate of an adjacent overlaying layer of the spirally wound portion.

In each spirally wound portion, a majority of the projections of the three-dimensional substrate in each layer may be at least partially nested with a majority of the projections of the three-dimensional substrate of an adjacent overlaying layer of the spirally wound portion once at least one layer of the three-dimensional substrate is wound upon the core.

The tension applied to the three-dimensional substrate during the spirally and helically winding steps, i.e. the force applied to the three-dimensional substrate to pull it when spooling may be less than 10%, preferably less than 5% of the elongation to break of the three-dimensional substrate of its original length in the machine and/or cross-machine directions at or before reaching the peak tensile force if subjected to the WSP 110.4 (09) Tensile Method.

The plane of the three-dimensional substrate may comprise a continuous land area.

A method of winding a three-dimensional substrate about a core to form a spool is provided. The three-dimensional substrate has a plane and comprises a plurality of projections extending outwardly from the plane of the three-dimensional substrate. The three-dimensional substrate is made from the group consisting of a nonwoven web, a film and combinations thereof. The core has a longitudinal axis and a length along the longitudinal axis. The core comprises first and second transversal side edges.

The method comprises the following steps:
(a) forming a first plurality of spirally wound portions and a first plurality of helically wound portions by:
 i) positioning an end of the three-dimensional substrate on the core;
 ii) spirally winding the three-dimensional substrate around the core to form each spirally wound portion of the first plurality of spirally wound portions; and wherein the spirally wound portions of the first plurality of spirally wound portions are located next to each other along the longitudinal axis of the core between the first transversal side edge of the core and the second transversal side edge of the core;

iii) helically winding the three-dimensional substrate around the core along the longitudinal axis of the core to form each helically wound portion of the first plurality of helically wound portions; and wherein each helically wound portion of the first plurality of helically wound portions extends between two adjacent spirally wound portions of the first plurality of spirally wound portions.

The three-dimensional substrate in each spirally wound portion of the first plurality of spirally wound portions is repeatedly and spirally wound around the core to form a plurality of layers overlaying each other. In each spirally wound portion, a majority of the projections of the three-dimensional substrate in at least some of the layers are at least partially nested with a majority of the projections of the three-dimensional substrate of an adjacent overlaying layer of the spirally wound portion.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

FIG. 1 is a schematic perspective view of a spool within the scope of the invention;

FIG. 2 is a schematic cross-sectional view of the spool taken about line 2-2 of FIG. 1;

FIG. 3 is a detailed view of a spirally wound portion of the spool of FIG. 1 showing a plurality of overlaying layers;

DETAILED DESCRIPTION OF THE INVENTION

Definitions

Figure 4:
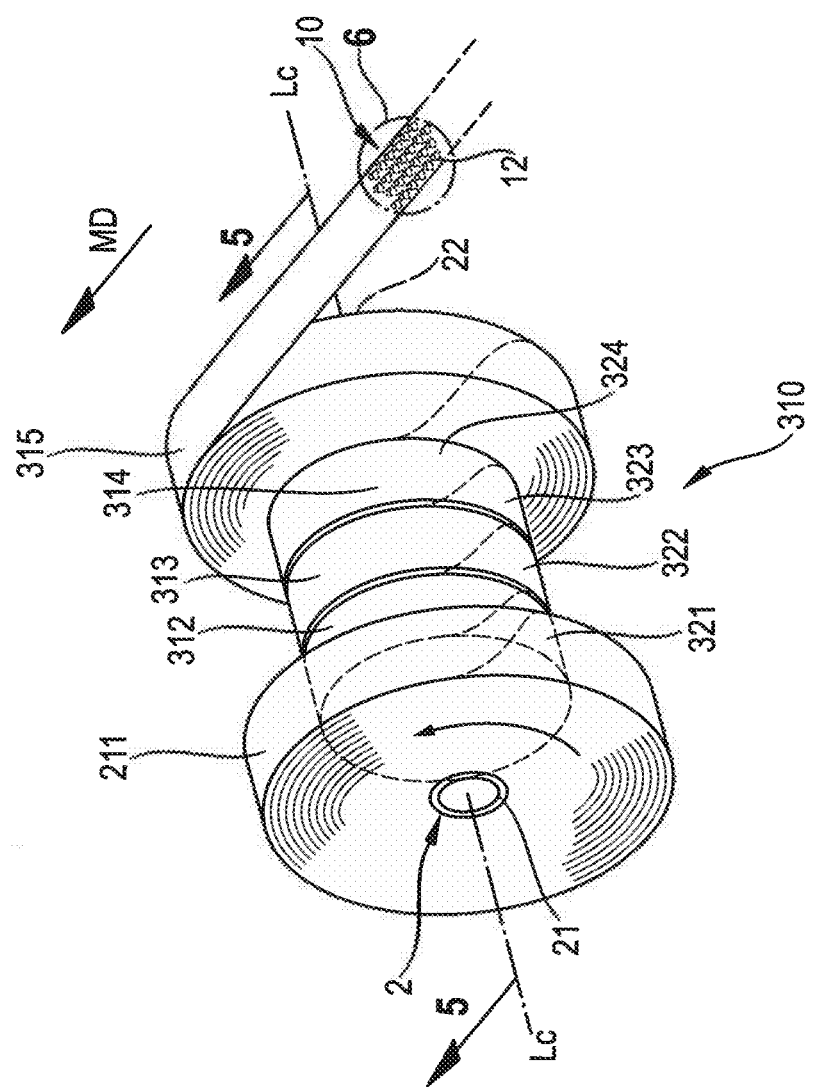
FIG. 4 is a schematic perspective view of a spool within the scope of the invention.

The term "absorbent article" as used herein refers to devices which absorb and contain bodily exudates, and, more specifically, refers to devices which are placed against or in proximity to the body of the wearer to absorb and contain the various exudates discharged from the body. Typical absorbent articles of the present invention include but are not limited to diapers, adult incontinence briefs, training pants, diaper holders and liners, absorbent inserts and the like, as well as feminine hygiene products, such as sanitary napkins and panty liners, and the like. Absorbent articles also include wipes, such as household cleaning wipes, baby wipes, and the like.

The term "caliper" as used herein means the thickness of a three-dimensional substrate under a defined load at 0.1 kPa.

The term "disposable" as used herein refers to absorbent articles which generally are not intended to be laundered or otherwise restored or reused (i.e., they are intended to be discarded after a single use and, preferably, to be recycled, composted or otherwise discarded in an environmentally compatible manner).

The term "machine direction" or "MD" as used herein means the direction parallel to the flow of the endless sheet of the three-dimensional substrate. The machine direction is substantially perpendicular to the longitudinal axis of the core.

The term "cross-machine direction" or "CD" as used herein means the path that is perpendicular to the machine direction in the plane of the web.

The term "film" as used herein refers to a substantially non-fibrous sheet-like material wherein the length and width of the material far exceed the thickness of the material. Typically, films have a thickness of 0.5 mm or less. Films may be configured to be liquid impermeable and/or vapor permeable (i.e., breathable).

The term "nonwoven web" as used herein means a manufactured sheet, web, or batt of directionally or randomly orientated fibers, bonded by friction, and/or cohesion, and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers may have diameters ranging from less than 0.001 mm to more than 0.2 mm and may come in several different forms such as short fibers (known as staple, or chopped), continuous single fibers (filaments or monofilaments), untwisted bundles of continuous filaments (tow), and twisted bundles of continuous filaments (yarn). Nonwoven webs may be formed by many processes such as meltblowing, spunbonding, solvent spinning, electrospinning, carding, and airlaying.

The term "projection" as used herein refers to a protrusion which protrudes outwardly from a plane of the three-dimensional substrate forming a base at the plane and a distal portion opposed from the plane. The opposed distal portion of the projection extends to a distal end which forms a top peak.

The term "recess" as used herein refers to a protrusion which protrudes inwardly from a plane of the three-dimensional substrate, i.e. in a direction opposite of a projection or which extends below the plane when viewing from the cross-section of the three-dimensional substrate. When the recess protrudes inwardly from the plane of the three-dimensional substrate, the recess forms a concave depression at the plane and an opposed distal portion from the plane. The opposed distal portion of the recess extends to a distal end which forms a base of the recess. A recess may comprise an aperture. The projections and recesses form a three-dimensional surface on a first surface of the three-dimensional substrate.

The term "spirally wound portion" as used herein refers to a portion of the spool in which the three-dimensional substrate is repeatedly and spirally wound around the core to form a plurality of layers overlaying each other. The three-dimensional substrate is being revolved around the core. The side edges of the layers of the plurality of layers of the three-dimensional substrate in the spirally wound portion may be substantially aligned with each other. The side edges of the layers of the plurality of layers of the three-dimensional substrate may be substantially perpendicular to the longitudinal axis of the core in other words. The term "spiral" is used in its normal geometrical definition where a spirally is a plane curve generated by a point moving along a straight line while the line revolves about a fixed point, here on the core.

The term "helically wound portion" as used herein refers to a portion of the spool in which the three-dimensional substrate is helically wound around the core along the longitudinal axis of the core. A helically wound portion extends between two adjacent spirally wound portions. The three-dimensional substrate passes from a first position, i.e. the uppermost layer of a first spirally wound portion to a second position, i.e. the lowermost layer of a second and adjacent spirally wound portion according to a helix motion, i.e. a screwing motion. The term "helical" is used in its normal geometrical definition where helically qualifies a space curve generated by a point moving along a straight line while the line revolves about another line, generally parallel to the first as an axis, i.e. the core.

The term "base of a projection" as used herein refers to the perimeter, preferably the circumference, where each projection starts to protrude outwardly from the plane of the three-dimensional substrate.

The term "at least partially nested" as used herein refers to a projection of a layer that coincides with and fits together with a projection of an adjacent overlaying layer. When two projections from two respective adjacent overlaying layers coincide with and fit together, the projections interlock with each other, i.e. nest with each other. The nested projections may not need to be fully aligned with each other along a z-directional axis of the three-dimensional substrate (i.e. partially nested).

The term "majority of projections" as used herein refers to more than 50% of the projections. Nested projections have a z-directional height from 500 to 4000 µm anywhere in the spool according to the Projection Height Test.

"Slightly collapsed projections" as used herein can be defined as having an average z-directional height with regard to the base which is reduced by more than 2% to 20% after winding and subsequent unwinding the three-dimensional substrate compared to the average z-directional height of the projections of the three-dimensional substrate measured before any winding of the three-dimensional substrate according to the Projection Height Test.

"Partially collapsed projections" as used herein can be defined as having an average z-directional height with regard to the base which is reduced by more than 20% to 40% after winding and subsequent unwinding the three-dimensional substrate the three-dimensional substrate compared to the average z-directional height of the projections of the three-dimensional substrate measured before any winding of the three-dimensional substrate according to the Projection Height Test.

"Completely collapsed projections" as used herein can be defined as having an average z-directional height with regard to the base which is reduced by more than 40% or more than 50% after winding and subsequent unwinding the three-dimensional substrate the three-dimensional substrate compared to the average z-directional height of the projections of the three-dimensional substrate measured before any winding of the three-dimensional substrate according to the Projection Height Test.

Spool—First Plurality

Figure 7:
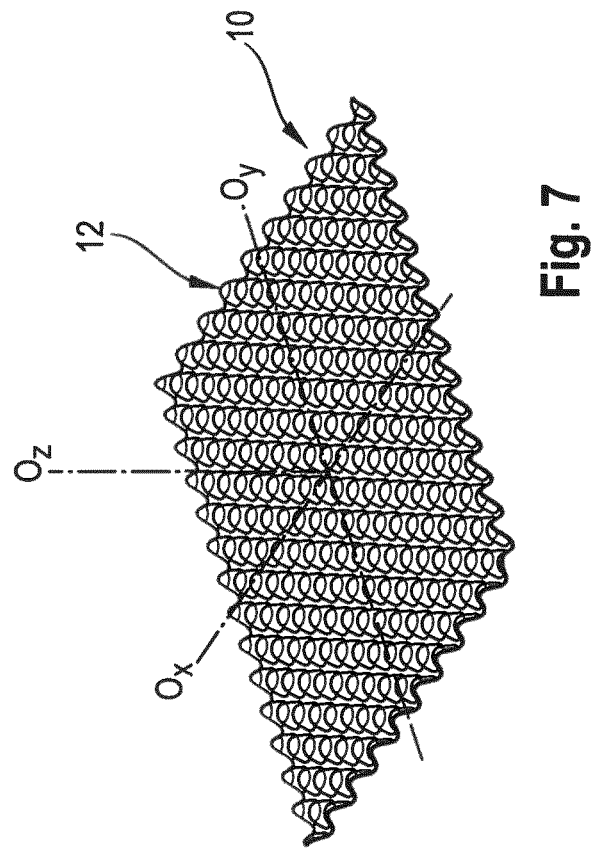
FIG. 7 is a top perspective view of the portion of the three-dimensional substrate of FIG. 6 in accordance with the present invention.
Figure 6:
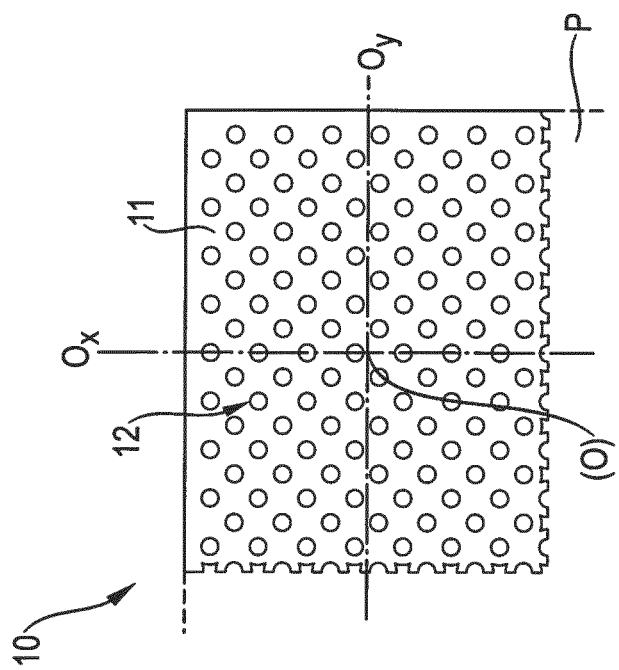
FIG. 6 is a top view of a portion of a three-dimensional substrate which can be wound around the core of the spool of FIG. 1, in accordance with the present invention.

A spool 1 comprising a three-dimensional substrate 10 and a core 2 is provided, as exemplary shown in FIGS. 1 and 2. The three-dimensional substrate has a plane P and comprises a plurality of projections 12 extending outwardly from the plane P of the three-dimensional substrate 10, as shown in FIGS. 6 and 7.

The spool 1 comprises a core 2 having a longitudinal axis Lc and a length along the longitudinal axis Lc. The core 2 comprises first and second transversal side edges 21, 22.

The spool 1 comprises a first plurality of spirally wound portions 110 and a first plurality of helically wound portions 120.

The three-dimensional substrate 10 is spirally wound around the core 2 to form all spirally wound portions 111, 112, 113, 114, 115 of the first plurality of spirally wound portions 110. All spirally wound portions (in combination) of the first plurality of spirally wound portions 110 may extend along the full length of the core 2 between the first and second transversal side edges 21, 22 of the core 2.

Alternatively, the three-dimensional substrate 10 may be spirally wound around the core 2 to form all spirally wound portions 111, 112, 113, 114, 115 of the first plurality of spirally wound portions 110 along a part of the length of the core 2 between the first and second transversal side edges 21, 22 of the core 2. Hence, the first plurality of spirally wound portions 110 may be spaced away from the first and/or second transversal side edges of the core 2. This can be useful when the core 2 has to be attached at a certain location (e.g. a support) of the manufacturing line.

The spirally wound portions 111, 112, 113, 114, 115 of the first plurality of spirally wound portions 110 are located next to each other along the longitudinal axis Lc of the core 2 between the first and second transversal side edges 21, 22 of the core 2.

Also, the three-dimensional substrate 10 is helically wound around the core 2 along the longitudinal axis Lc to form each helically wound portion 121, 122, 123, 124 of the first plurality of helically wound portions 120. Each helically wound portion of the first plurality of helically wound portions 120 extends between two adjacent spirally wound portions of the first plurality of spirally wound portions 110. The helically wound portions of the first plurality of helically wound portions 120 may comprise a plurality of overlaying layers. Alternatively, the helically wound portions of the first plurality of helically wound portions 120 may comprise a single layer of the three-dimensional substrate 10.

The three-dimensional substrate 10 in each spirally wound portion of the first plurality of spirally wound portions 110 is repeatedly and spirally wound around the core 2 to form a plurality of layers overlaying each other.

In other words, the three-dimensional substrate 10 has been wound for a given number of revolutions in each spirally wound portion and then traversed (i.e. displaced along the core 2) to form the subsequent spirally wound portion.

In each spirally wound portion, a majority of the projections of the three-dimensional substrate 10 in at least some of the layers are at least partially nested with a majority of the projections of the three-dimensional substrate 10 of an adjacent overlaying layer of the spirally wound portion.

In each spirally wound portion, a majority of the projections of the three-dimensional substrate 10 in each layer may be at least partially nested with a majority of the projections of the three-dimensional substrate 10 of an adjacent overlaying layer of the spirally wound portion.

Between two adjacent and overlaying layers of a spirally wound portion, the projections of the respective layers can fit and coincide together. More than 50% or more than 60% or more than 70% or more than 80% or more than 90% of the projections of a layer can nest with the projections of the adjacent overlaying layer of each spirally wound portion.

By having a majority of the projections of a layer at least partially nested with a majority of the projections of an adjacent overlaying layer, the majority of the projections of the three-dimensional substrate 10 are thus preserved.

The following passages related to the tension applied on the three-dimensional substrate are equally applicable to the second, third and other plurality of spirally wound portions (if present) and helically wound portions of the spool 1.

In order to get a majority of the projections 12 of the three-dimensional substrate 10 nested, the three-dimensional substrate 10 may have a certain tension which is applied during the spooling process, i.e. during the spirally and helically winding steps. The tension represents the force applied to the three-dimensional substrate 10 to pull it when spooling. The tension should not be excessively high to avoid permanent deformations, thus losing the three-dimensional projections 12.

The three-dimensional substrate 10 comprises a longitudinal axis and a length. The length of the three-dimensional substrate 10 can be measured along the longitudinal axis of the three-dimensional substrate 10. The longitudinal axis of the three-dimensional substrate 10 is substantially parallel to the MD direction when the three-dimensional substrate 10 is attached and wound upon the core 2. The tension applied to the three-dimensional substrate 10 may be less than 10%, preferably less than 5% of the elongation to break of the three-dimensional substrate 10 of its original length in the machine direction MD at or before reaching the peak tensile force if subjected to the Standard Tensile Test Method WSP 110.4 (09).

The tension applied to the three-dimensional substrate 10 in the machine direction MD has been found to help nesting of projections. Indeed, a relatively low tension applied to the three-dimensional substrate 10 can help to stretch the projections 12 without any irreversible deformations. Being slightly stretched, the projections of adjacent overlaying layers have been found to have the tendency to slightly shift and rearrange in order to coincide and nest together. Having nested projections can help the three-dimensional substrate 10 to reach a more stable state, i.e. a lower energy state.

The first plurality of spirally wound portions 110 may comprise from 3 to 30 spirally wound portions or from 3 to 10 spirally wound portions or from 3 to 5 spirally wound portions.

The spool 1 may only comprise the first plurality of spirally wound portions 110 and the first plurality of helically wound portions 120. Each spirally wound portion 111, 112, 113, 114, 115 may have a diameter from 0.5 m to 2.0 m, or from 0.8 m to 1.5 m or from 0.8 m to 1.2 m.

The diameter may be measured from the center of the core in a radially direction substantially perpendicular to the longitudinal axis Lc of the core 2. The diameter of each spirally wound portion of the first plurality of spirally wound portions 110 may be the same or may differ from each other.

Each spirally wound portion of the first plurality of wound portions 110 has a relatively high number of layers as compared to the number of layers within the helically wound portion extending between two adjacent spirally wound portions of the first plurality of spirally wound portions 110. Indeed, each of the helically wound portions of the spool 1 may include from 0.20 to 5 layers or from 0.25 to 1 layer of the three-dimensional substrate 10 wound around the core 2. Each of the helically wound portions of the spool 1 may include different numbers of layers from each other.

It has been found that when the three-dimensional substrate 10 follows a helix path all the time, the projections 12 of the three-dimensional substrate 10 could not nest appropriately.

Within a helically wound portion 121 of the first plurality of helically wound portions 120, the three-dimensional substrate 10 is drawn from an uppermost layer of the adjacent spirally wound portion 111 towards the core 2 following a helix path. The motion and path followed by the three-dimensional substrate 10 to be drawn towards the core 2 may create wrinkles, twists and folds in the three-dimensional substrate 10 within the layers comprised within the helically wound portion. Hence, the projections of the three-dimensional substrate comprised within each helically wound portion of the first plurality of helically wound portions 120 could not be ideally preserved.

Minimizing the content of the helically wound portions can help to better preserve the three-dimensional features of the projections 12 of the three-dimensional substrate 10. The helically wound portions of the first plurality of helically wound portions 120 may only comprise from 0.01% to 10% or from 1% to 10% of the total amount of the three-dimensional substrate 10 wound in the spool 1.

Each of the helically wound portions may include as few layers of the three-dimensional substrate 10 as possible in order to minimize the amount of non-nested projections of the three-dimensional substrate 10. Each of the helically wound portions of the spool 1 may include from 0.20 to 5 layers or from 0.25 to 1 layer of the three-dimensional substrate 10 wound around the core 2, i.e. a helically wound portion may not have a layer of the three-dimensional substrate 10 fully extending around the core 2.

Spool—Second Plurality

Figure 5:
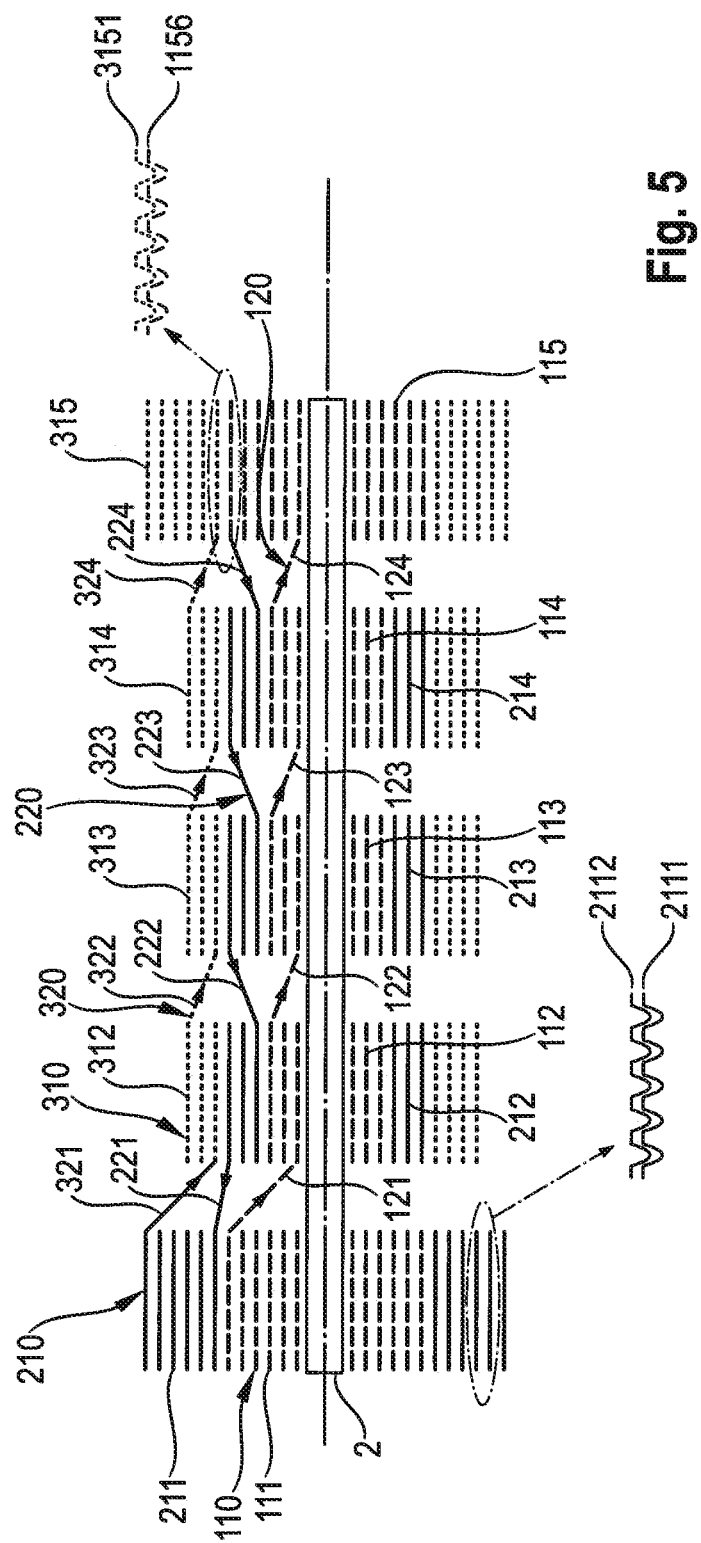
FIG. 5 is a schematic cross-sectional view of the spool taken about line 5-5 of FIG. 4.

The spool 1 may comprise a second plurality of spirally wound portions 210 and a second plurality of helically wound portions 220, as exemplary shown in FIGS. 4 and 5.

The three-dimensional substrate 10 may be spirally wound around some or all but one of the first plurality of spirally wound portions 110 to form one or more spirally wound portions of the second plurality of spirally wound portions 210.

The three-dimensional substrate 10 may be spirally wound around the first plurality of spirally wound portions 110 to form each spirally wound portion 211, 212, 213, 214 of the second plurality of spirally wound portions 210. The spirally wound portions 211, 212, 213, 214 may be located next to each other along the longitudinal axis Lc of the core 2 between the second transversal side edge 22 of the core 2 and the first transversal side edge 21 of the core 2.

The three-dimensional substrate 10 in each spirally wound portion 211, 212, 213, 214 of the second plurality of spirally wound portions 210 may be repeatedly and spirally wound around the core 2 along the longitudinal axis Lc of the core 2 in a direction opposite of the first plurality of spirally wound portions 110, i.e. from the second transversal side edge 22 of the core 2 to the first transversal side edge 21 of the core 2.

Also, the three-dimensional substrate 10 may be helically wound around the first plurality of spirally wound portions 110 to form each helically wound portion 221, 222, 223, 224 of the second plurality of helically wound portions 220.

As a result, as shown in a schematic cross-sectional view in a FIG. 5, from the first transversal side edge 21 to the second transversal side edge 22 of the core 2, each helically wound portion of the first plurality of helically wound portions 120 extends between an uppermost layer of spirally wound portion to a lowermost layer of the adjacent spirally wound portion. Each helically wound portion of the second plurality of helically wound portions 220 extend between a lowermost layer of spirally wound portion to an uppermost layer of the adjacent spirally wound portion.

The first helically wound portion 224 of the second plurality of helically wound portions 220 extends between the last spirally wound portion 115 of the first plurality of spirally wound portions 110 and the first spirally wound portion 214 of the second plurality of spirally wound portions 210. The other helically wound portion 221, 222, 223 of the second plurality of helically wound portions 220 extends between two adjacent spirally wound portions of the second plurality of spirally wound portions 210.

The spool 1 may comprise a third plurality of spirally wound portions 310 and a third plurality of helically wound portions 320, as exemplary shown in FIG. 5. The third plurality of helically wound portions 320 may have the same orientation as the first plurality of helically wound portions 120.

The first helically wound portion 321 of the third plurality of helically wound portions 320 extends between the last spirally wound portion 211 of the second plurality of spirally wound portions 210 and the first spirally wound portion 312 of the third plurality of spirally wound portions 310. The other helically wound portion 322, 323, 324 of the third plurality of helically wound portions 320 extends between two adjacent spirally wound portions of the third plurality of spirally wound portions 310.

Hence, the three-dimensional substrate 10 is wound around the core 2 such that the first, second, third, etc. plurality of spirally wound portions go back and forth between first and second transversal side edges 21, 22 of the core 2. This can help to wind a greater length of three-dimensional substrate 10 around the core 2 while the projections 12 of the three-dimensional substrate 10 are preserved.

In each spirally wound portion, a majority of the projections of the three-dimensional substrate 10 in at least some of the layers are at least partially nested with a majority of the projections of the three-dimensional substrate 10 of an adjacent overlaying layer of the spirally wound portion (See for example the overlaying layers 2112, 2111 of the spirally wound portion 211 of the spool 1 in FIG. 5).

In each spirally wound portion, a majority of the projections of the three-dimensional substrate 10 in each layer may be at least partially nested with a majority of the projections of the three-dimensional substrate 10 of an adjacent overlaying layer of the spirally wound portion, as exemplary illustrated in FIG. 3.

As exemplary shown in FIG. 3, the layers 1111, 1112, 1113 of the spirally wound portion 111 of the first plurality of spirally wound portions 110 are overlaying each other. The projections of the three-dimensional substrate 10 in each layer are nested with the projections of the three-dimensional substrate 10 of an adjacent overlaying layer of the spirally wound portion 111.

Between two adjacent and overlaying layers of a spirally wound portion, the projections of the respective layers can fit and coincide together. More than 50% or more than 60% or more than 70% or more than 80% or more than 90% of the projections of a layer can nest with the projections of the adjacent overlaying layer of each spirally wound portion.

By having a majority of the projections of a layer at least partially nested with a majority of the projection of an adjacent overlaying layer, the majority of the projections of the three-dimensional substrate 10 are thus preserved.

A majority of the projections of the three-dimensional substrate 10 of the uppermost layer of a spirally wound portion 111 of the first plurality of spirally wound portions 110 may be at least partially nested with a majority of the projections of the three-dimensional substrate 10 of the lowermost layer of the spirally wound portion 211 of the second plurality of spirally wound portions 210 which is positioned directly above the respective spirally wound portion 111 of the first plurality of spirally wound portions 110.

A majority of the projections of the three-dimensional substrate 10 of the uppermost layer of a spirally wound portion 115 of the first plurality of spirally wound portions 110 may be at least partially nested with a majority of the projections of the three-dimensional substrate 10 of a lowermost layer of the spirally wound portion 315 of another plurality of spirally wound portions, e.g. the third plurality of spirally wound portions 310 which is positioned directly above the respective spirally wound portion 115 of the first plurality of spirally wound portions 110 (See for example the overlaying layers 3151, 1156 of the respective spirally wound portions 315, 115 of the spool 1 in FIG. 5).

For two pluralities of spirally wound portions, the last spirally wound portion 115 of the first plurality of spirally wound portions 110 and the first spirally wound portion 214 of the second plurality of spirally wound portions 210 will be adjacent to each other along the longitudinal axis Lc of the core 2 (i.e. they are not overlaying each other). The same applies between the second, third and additional pluralities of spirally wound portions 210, 310.

More than 50% of the projections of an uppermost layer of a spirally wound portion can nest with more than 50% of the projections of the adjacent lowermost layer of an adjacent spirally wound portion (i.e. the one below).

Two adjacent spirally wound portions may be separated by a gap. The gap between two adjacent spirally wound portions may be from 1 mm to 10 mm or from 2 mm to 5 mm.

If there is a gap, each helically wound portion may partially or completely fill the gap between two adjacent spirally wound portions disposed one next to the other in the direction substantially parallel to the longitudinal axis Lc of the core 2. Each of the helically wound portions of the spool may include from 0.20 to 5 layers or from 0.25 to 1 layer of the three-dimensional substrate 10 wound around the core 2 or the first plurality of spirally wound portions 110.

The total number of helically wound portions of the spool 1 may represent from 1% to 30% or from 1% to 15% or from 1% to 10% or from 1% to 5% of the total amount of three-dimensional substrate 10 wound in the spool 1. In order to decrease this amount of helically wound portions in the spool 1, the number of overlaying layers in each spirally wound portions may be increased while each of the helically wound portions of the spool may include a relatively low number of layers of the three-dimensional substrate 10 wound around the core 2 or the first plurality of spirally wound portions 110. By having a small proportion of the three-dimensional substrate 10 wound in the helically wound portions, the projections of the three-dimensional substrate 10 can thus be better preserved.

When the spool 1 only comprises a first plurality of spirally wound portions 110 and a first plurality of helically wound portions 120, each spirally wound portion of the first plurality of spirally wound portions 110 may comprise a relative high number of layers compared to the number of layers within each helically wound portion. However, when a spirally wound portion reaches a diameter such as 1 m or more, the three-dimensional substrate 10 has to traverse a relatively large distance from the uppermost layer of the spirally wound portion to the adjacent spirally wound portion, i.e. to the next adjacent position at the core 2. The height between the uppermost layer of the spirally wound portion and the core may be relatively high so as to require slowing down the winding process in order to better control the change of the position of the three-dimensional substrate 10. Otherwise, if the speed to achieve the helix motion remains relatively high, it might occur that the spirally wound portion (from which the helically wound portion starts) may collapse on the core 2.

By having a second, third, or more pluralities of spirally wound portions and a second, third, or more pluralities of helically wound portions, the number of layers in each spirally wound portions can be reduced while still providing a sufficient overall length of the three-dimensional substrate 10 on the spool. As a result, the process step required to get the three-dimensional substrate 10 traversed along the longitudinal axis Lc of the core 2 in the helically wound portion can be done at relatively high speeds. This can provide an improved process stability and reliability.

Each spirally wound portion of each plurality of spirally wound portions positioned adjacent to the first or second transversal side edge 21, 22 of the core 2 may have a higher number of layers than the other spirally wound portions of each plurality of spirally wound portions of the spool 1. Having a relatively high number of overlaying layers at or adjacent to first and second transversal side edges 21, 22 of the core 2 rather than in the other locations of the spool can provide some stability at the transversal side edges 21, 22 of the core 2. Improved stability at the transversal side edges 21, 22 of the core 2 can facilitate the transportation of the converted spools.

The side edges of the layers of the plurality of layers of the three-dimensional substrate 10 in each spirally wound portion may be substantially aligned with each other. This also can help to provide stability of each spirally wound portion and thus of the final spool 1.

Three-Dimensional Substrate

The three-dimensional substrate 10 is made from the group consisting of a nonwoven web, a film and combinations thereof.

The three-dimensional substrate 10 is formed by one or more nonwoven webs. The three-dimensional substrate 10 may be formed by a laminate comprising one or more nonwoven webs and one or more other materials, such as films or cellulosic materials. Combining a nonwoven web and a film will form a laminate.

The nonwoven web may be a carded nonwoven, spunbond nonwoven ("S") or meltblown nonwoven ("M"), or laminates of any of these. For example spunmelt polypropylene nonwovens are suitable, in particular those having a laminate web SMS, or SMMS, or SSMMS, structure. Suitable materials are for example disclosed in U.S. Pat. No. 7,744,576; US2011/0268932A1; US2011/0319848A1 or US2011/0250413A1. Nonwoven materials provided from synthetic fibers may be used, such as polyethylene (PE), polyethylene terephthalate (PET) and in particular polypropylene (PP).

The nonwoven web may be made of cellulosic fibers. The nonwoven web may have a basis weight range from 5 gsm to 50 gsm or from 5 gsm to 15 gsm.

Alternatively, the three-dimensional substrate 10 is formed by a film. A film may comprise any known material being moisture pervious, liquid pervious or liquid impervious. An impervious film may be rendered pervious by being microporous or apertured.

The three-dimensional substrate 10 may comprise a plurality of projections having a first z-directional height. Each projection protrudes outwardly from the plane P of the three-dimensional substrate 10 forming a base and an opposed distal portion from the plane P. The distal portion of the projection extends to a distal end which forms a top peak which is spaced away from the base of the projection. The base of each projection can be defined as the perimeter, which for circular projections, is the circumference, where each projection 12 starts to protrude outwardly from the plane P of the three-dimensional substrate 10.

The three-dimensional substrate 10 comprises the plurality of projections 12 extending outwardly from the plane P of the three-dimensional substrate 10. The plurality of projections 12 of the three-dimensional substrate 10 may form a three-dimensional surface on a first surface of the three-dimensional substrate 10. The projections of the plurality of projections can be hollow. When viewing from the first surface of the three-dimensional substrate 10, a plurality of projections 12 protrude from the plane P of the three-dimensional substrate 10. All the projections protrude from the plane in the same direction, as shown in FIGS. 6 and 7.

The plurality of projections 12 may be surrounded by a plurality of land areas 11 of the three-dimensional substrate 10.

In addition to the plurality of land areas 11 and the plurality of projections 12, the three-dimensional substrate 10 may comprise a plurality of recesses 13 on the first surface of the three-dimensional substrate 10.

Figure 9:
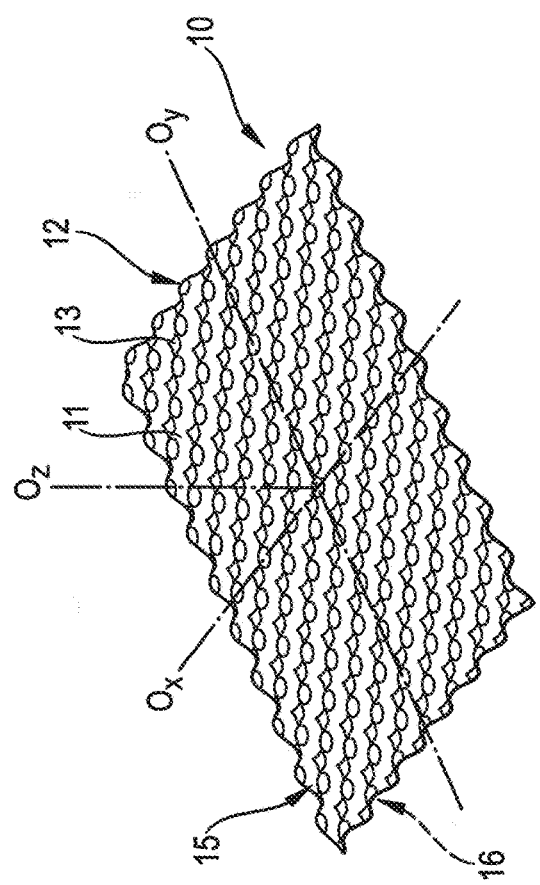
FIG. 9 is a top perspective view of the portion of the three-dimensional substrate of FIG. 8 in accordance with the present invention.
Figure 8:
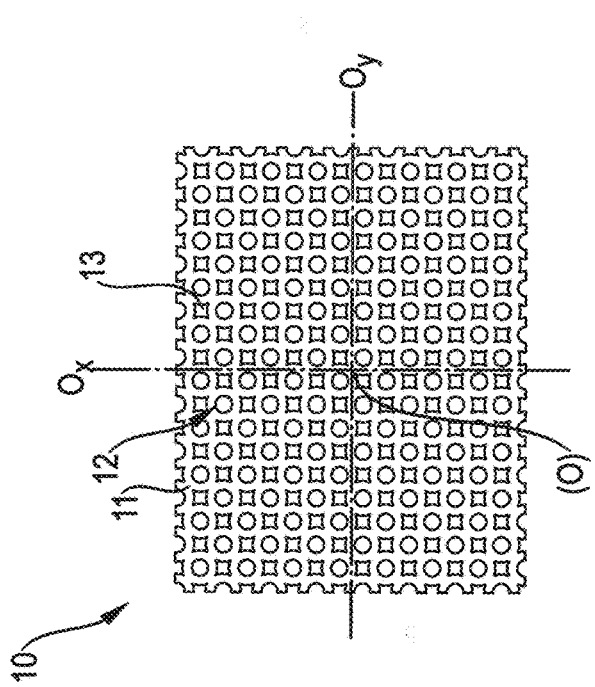
FIG. 8 is a top view of a portion of a three-dimensional substrate, in accordance with the present invention.

When viewing from the first surface of the three-dimensional substrate 10, the three-dimensional substrate 10 may comprise a plurality of projections 12 alternating with a plurality of recesses 13, as shown in FIGS. 8 and 9.

The three-dimensional substrate 10 may comprise a plurality of land areas 11, a plurality of recesses 13, and a plurality of projections 12. The plurality of land areas 11, the plurality of recesses 13, and the plurality of projections 12 may together form a three-dimensional surface on the first surface 15 of the three-dimensional substrate 10.

As exemplary shown in FIGS. 8 and 9, the plane P of the three-dimensional substrate 10 may comprise a continuous land area.

The three-dimensional substrate 10 may have the following repetitive grid pattern when viewing the three-dimensional substrate 10 from the first surface 15 of the three-dimensional substrate: Each projection 12 of the three-dimensional substrate 10 may be positioned at a center of a square wherein each corner of the square includes a further projection 12.

If the three-dimensional substrate 10 also comprises a plurality of recesses 13, each recess 13 may be positioned substantially at the center of each edge of the square. The plurality of land areas 11 may then encompass the space between the plurality of projections 12 and the plurality of recesses 13.

The projections 12 may be generally dome-shaped when viewing from the first surface 15 of the three-dimensional substrate 10 and may be hollow arch-shaped when viewing from the opposite second surface 16 of the three-dimensional substrate 10.

The projections 12 may alternate with the recesses 13 in a direction generally perpendicular with the longitudinal axis of the three-dimensional substrate 10. The projections 12 may also alternate with the recesses 13 in a direction generally parallel with a longitudinal axis of the three-dimensional substrate 10.

Two or more adjacent projections 12 may be separated from each other by a recess 13 and one or more land areas 11 in a direction generally perpendicular to the longitudinal axis or in a direction generally parallel to the longitudinal axis of the three-dimensional substrate 10.

Two or more adjacent recesses 13 may be separated by a projection 12 and one or more land areas 11 in a direction generally perpendicular to the longitudinal axis or in a direction generally parallel to the longitudinal axis of the three-dimensional substrate 10. The land areas 11 may fully surround the recesses 13 and the projections 12. The land areas 11 may together form a generally continuous grid through the three-dimensional substrate 10, while the projections 12 and the recesses 13 may be discrete elements throughout the three-dimensional substrate 10 according to the repetitive grid pattern as defined above.

Each recess 13 of the plurality of recesses may comprise an aperture. Advantageously, the aperture may be located at the base of the recess.

The projections 12 extending outwardly from the plane of the three-dimensional substrate 10 may represent at least 20% or at least 30% or at least 40% of the total area of the three-dimensional substrate 10.

The projections 12 extending outwardly from the plane of the three-dimensional substrate 10 may represent no more than 70% or no more than 60% or no more than 50% of the total area of the three-dimensional substrate 10.

The projections 12 of the three-dimensional substrate 10 may have a z-directional height from 500 µm to 4000 µm or from 300 µm to 3000 µm or from 500 µm to 3000 µm or from 800 µm to 1400 µm or from 1100 µm to 1200 µm. The z-directional height of the projections 12 of the three-dimensional substrate 10 is measured according to the Projection Height Test described herein.

The recesses 13 of the three-dimensional substrate 10 may have a z-directional height from 100 µm to 3000 µm or from 300 µm to 2000 µm or from 500 µm to 1500 µm or from 700 µm to 1000 µm. The z-directional height of the recesses of the three-dimensional substrate 10 is measured according to the Recess Height Test described herein.

The three-dimensional substrate 10, or portions thereof, may have an overall z-directional height from 700 µm to 6000 µm or from 750 µm to 4000 µm or from 1000 µm to 2500 µm or from 1750 µm to 2300 µm anywhere in the spool 1. The overall z-directional height of the three-dimensional substrate 10, or portions thereof, is measured according to the Overall Substrate Height Test described herein.

The three-dimensional substrate 10 taken from the spool 1 may have a dry caliper from 500 µm to 4000 µm at 0.1 kPa according to the Dry Caliper Test Method.

The three-dimensional substrates of the present invention may comprise one or more colors, dyes, inks, indicias, patterns, embossments, and/or graphics. The colors, dyes, inks, indicias, patterns, and/or graphics may aid the aesthetic appearance of the three-dimensional substrates.

The three-dimensional substrates of the invention may be used as a portion of, or all of, any suitable products, such as disposable absorbent articles, for example as a topsheet, wipe (wet or dry), toilet tissue, or any other suitable products.

Figure 10:
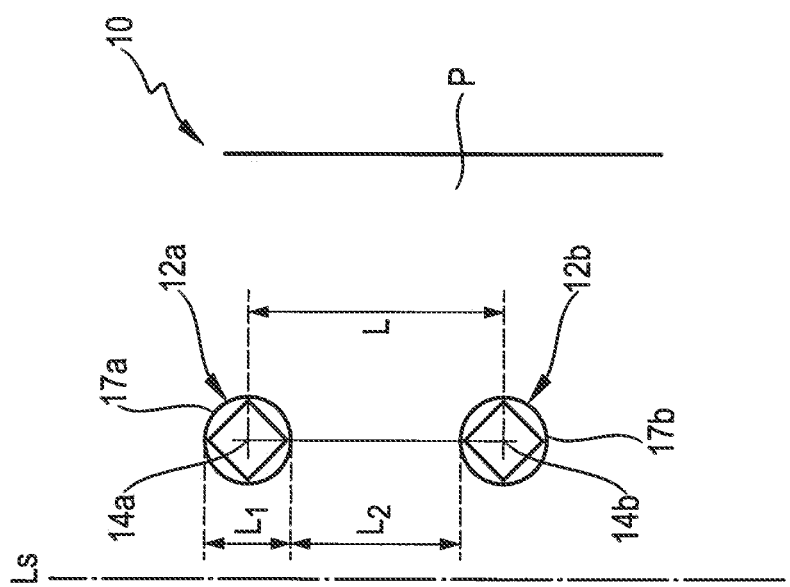
FIG. 10 is a portion of the front view of FIG. 6 showing two neighboring projections aligned in a direction substantially parallel along a longitudinal axis of the three-dimensional substrate.

FIG. 10 is a portion of the front view of FIG. 6 showing two neighboring projections 12A, 12B aligned in a direction substantially parallel along a longitudinal axis Ls of the three-dimensional substrate 10.

A notional circle 17A, 17B may be drawn around the base of each projection 12A, 12B which is as small as possible without intersecting the perimeter of the base of each projection 12A, 12B (while it may coincide with portions— or all—of the perimeter). E.g. the notional circle 17A, 17B may be coincident with the perimeter of circular projections 12A, 12B. Each notional circle 17A, 17B of each projection 12A, 12B may comprise a center 14A, 14B. Two neighboring projections may be aligned in a direction substantially parallel to a machine direction. The machine direction may be substantially parallel to the longitudinal axis Ls of the three-dimensional substrate 10.

The distance between the centers 14A, 14B of the notional circles 17A, 17B of the respective neighboring projections 12A, 12B may have a length L. The diameter of the circle 17A, 17B of one of the neighboring projections 12A, 12B may have a length L1. The minimum distance between the circumferences of the notional circles 17A, 17B of the respective neighboring projections 12A, 12B may have a length L2. The ratio of L1:L may be at least 0.3 and the ratio of L2:L may be such that $0 \leq L2:L \leq 0.7$ or $0 \leq L2:L \leq 0.5$.

Without being bound by theory, it is believed that when two neighboring projections 12A, 12B are defined by the ratio of L1:L being at least 0.3 and the ratio of L2:L being such that $0 \leq L2:L \leq 0.7$, the likelihood that the projections 12 between adjacent overlaying layers from one or more spirally wound portions will nest is increased. Indeed, when the projections 12 are sufficiently close to each other, it would require less energy to slightly shift and rearrange them in order to nest. These ratios may also be taken into consideration for the tension applied to the three-dimensional substrate 10 as set out above.

As a result, the tension applied to the three-dimensional substrate 10 and also the pattern selected for the plurality of projections 12 of the three-dimensional substrate 10, i.e. the ratios L1:L, L2:L can promote the rearrangement of the projections of overlaying layers of the three-dimensional substrate 10 in order to get the projections coincided and fitted together.

The distance L between the centers 14A, 14B of the notional circles 17A, 17B of the respective neighboring projections 12A, 12B may be from 2 mm to 15 mm or from 3 mm to 10 mm or from 3 mm to 5 mm. The length L1 may be from 2 mm to 15 mm or from 3 mm to 10 mm or from 3 mm to 5 mm.

Symmetry

Figure 11:
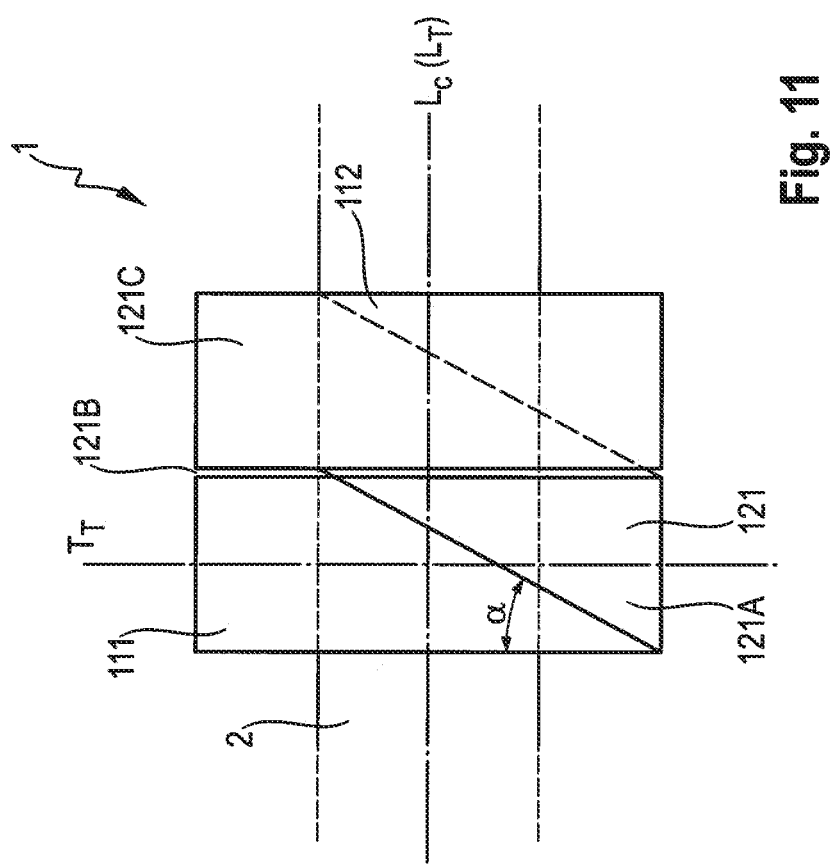
FIG. 11 is a front view of two spirally wound portions of a three-dimensional substrate being connected by a helically wound portion, wherein the angular extent and position of the helically wound portion have been deformed in order to provide an illustration of the spool that is visually comprehensible in a two dimensional form.

FIG. 11 is a front view of two spirally wound portions 111, 112 of a three-dimensional substrate 10 being connected by a helically wound portion 121. The angular extent and position of the helically wound portion have been deformed in order to provide an illustration of the spool that is visually comprehensible in a two dimensional form.

Each spirally wound portion may have a longitudinal axis Lt substantially parallel to the longitudinal axis Lc of the core 2 and a transversal axis Tt perpendicular to the longitudinal axis of the spirally wound portion. Each helically wound portion may form an angle α from 0.3 degrees to 60 degrees or from 2 degrees to 45 degrees or from 5 degrees to 40 degrees or from 10 degrees to 35 degrees relative to the transversal axis Tt of an adjacent spirally wound portion.

Each helically wound portion may comprise first, second and third areas 121A, 121B, 121C. The first area 121A may overlap with an uppermost layer of the spirally wound portion 111. The second area 121B may partially fill the gap between two adjacent spirally wound portions 111, 112. The third area 121C may overlap with the respective lowermost layer of the adjacent spirally wound portion 112.

In that case, the projections 12 of the three-dimensional substrate 10 in the second area 121B cannot nest due to the helix motion of the three-dimensional substrate 10. Concerning the projections 12 of the three-dimensional substrate 10 in the first and third areas 121A, 121C, slightly, partially or completely collapsed projections are observed.

The slightly or partially or completely collapsed projections are due to the fact the projections 12 in the first and third areas 121A, 121C of the helically wound portion 121 nest to a lower extent than the projections of adjacent overlaying layers of a spirally wound portion. This is due to the helical orientation of the helically wound portion 121 relative to each adjacent spirally wound portion 111, 112. Each spirally wound portion comprises from 2 to 4 times less collapsed projections than a helically wound portion.

A pattern is provided to improve the nesting of the projections 12 of the three-dimensional substrate 10 in the first and third areas 121A, 121C of the helically wound portion 121.

The plurality of projections 12 of the three-dimensional substrate 10 may form a repetitive pattern. The repetitive pattern may be characterized by a quasi-symmetry.

Figure 12:
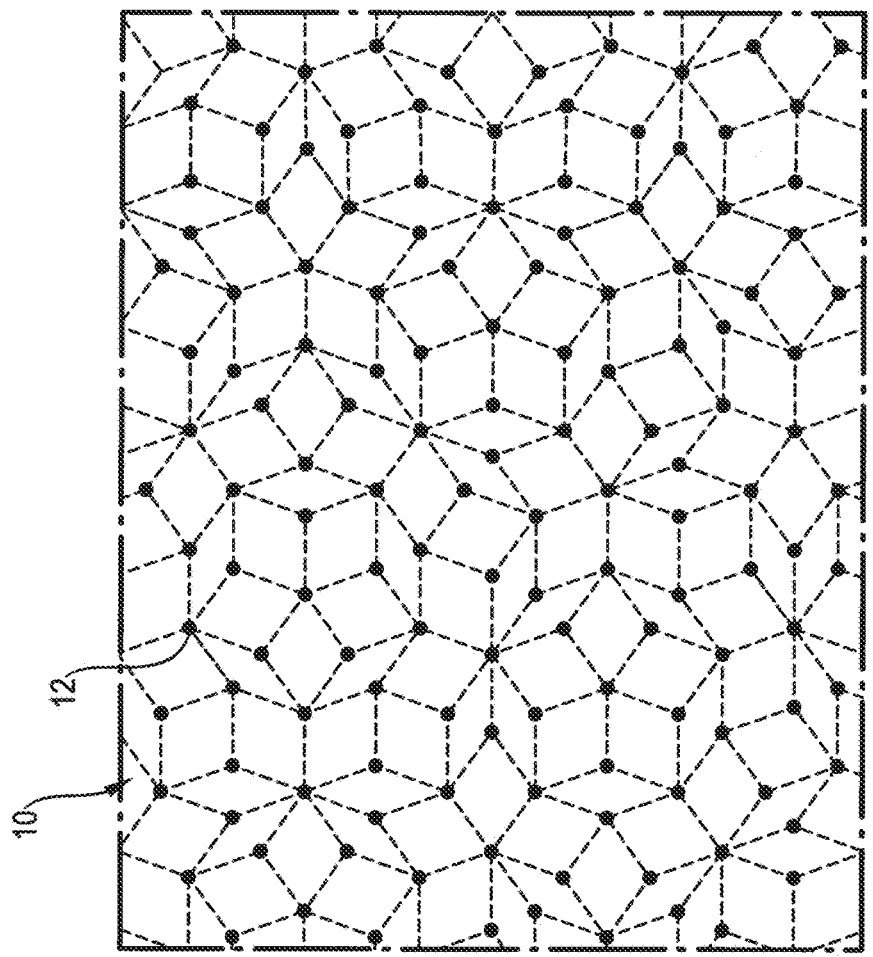
FIG. 12 is a top perspective view of the portion of the three-dimensional substrate wherein the repetitive pattern is a Penrose tiling type pattern.

Quasi-symmetry is defined by a pattern that is ordered but not periodic. A quasi-symmetric pattern may continuously fill all the plane P of the three-dimensional substrate 10, but it lacks translational symmetry, which means that a shifted copy of the pattern will never match exactly with its original. An example of such quasi-symmetric pattern for the three-dimensional substrate 10 may be a so-called Penrose tiling, as exemplary shown in FIG. 12. In that case, the projections 12 of the three-dimensional substrate 10 can be organized to form a Penrose tiling type pattern or any other desired quasi-symmetric pattern.

With a quasi-symmetric repetitive pattern, there will be zones in the first and third areas 121A, 121C of the helically wound portion than can nest with the respective uppermost and lowermost layers of the respective adjacent spirally wound portions.

Alternatively, the repetitive pattern may be characterized by its ability to keep its symmetry over a rotational symmetry according to an angle of less than 90 degrees or from 0.3 degrees to 45 degrees or from 2 degrees to 40 degrees or from 10 degrees to 35 degrees. As a result, the projections 12 of the three-dimensional substrate 10 in the first and third areas of the helically wound portions can nest with the respective uppermost and lowermost layers of the respective adjacent spirally wound portions.

In other words, the repetitive pattern may be selected such that when the helically wound portion forms an angle α relative to the transversal axis Tt of an adjacent spirally wound portion, the repetitive pattern may have its symmetry preserved upon a rotational symmetry according to the same angle α. The angle α may be less than 90 degrees, preferably from 0.3 degrees to 60 degrees or from 2 degrees to 45 degrees or from 5 degrees to 40 degrees or from 10 degrees to 35 degrees.

As described above, the three-dimensional substrate 10 may comprise a plurality of projections 12 and a plurality of land areas 11 wherein the land areas 11 surround the projections 12.

The plurality of projections 12 of the three-dimensional substrate 10 may form a repetitive unit comprising a polygon, preferably a regular convex polygon. The polygon may be defined as having n sides, n corners and a center. Each projection 12 of the plurality of the projections may be positioned at each corner of the polygon. Each helically wound portion 121 may form an angle α=360/n relative to the transversal axis Tt of an adjacent spirally wound portion 111, 112 such that the projections 12 of the three-dimensional substrate 10 in each helically wound portion 121 may be at least partially nested with the projections 12 of an adjacent overlaying layer of the three-dimensional substrate 10 comprised in each spirally wound portion 111, 112 adjacent to the helically wound portion 121. The number n for the n sides or n corners can be more than 6 or more than 8. The number n for the n sides or n corners can be up to 40 or up to 70 or up to 120 or up to 180.

As described above, the three-dimensional substrate 10 may comprise a plurality of recesses 13. The plurality of projections 12 and/or the plurality of recesses 13 of the three-dimensional substrate 10 may form a repetitive unit comprising a polygon, preferably a regular convex polygon. The polygon may be defined as having n sides, n corners and a center. Either each recess 13 of the plurality of the recesses or each projection 12 of the plurality of the projections may be positioned at each corner of the polygon while a projection 12 of the plurality of the projections or a recess 13 of the plurality of the recesses may be respectively positioned at the center of the polygon. Each helically wound portion 121 may form an angle α=360/n relative to the transversal axis Tt of an adjacent spirally wound portion 111, 112 such that the projections 12 of the three-dimensional substrate 10 in each helically wound portion 121 may be at least partially nested with the projections 12 of an adjacent overlaying layer of the three-dimensional substrate 10 comprised in each spirally wound portion 111, 112 adjacent to the helically wound portion 121.

The number n for the n sides or n corners can be more than 6 or more than 8. The number n for the n sides or n corners can be less than 40 or less than 30.

Also, the recess 13 of the three-dimensional substrate 10 in each helically wound portion 121 may be at least partially coincided with the recess 13 of an adjacent overlaying layer of the three-dimensional substrate 10 comprised in each spirally wound portion 111, 112 adjacent to the helically wound portion 121.

The recess 13 of the three-dimensional substrate 10 in a layer of each spirally wound portion 111 may be at least partially coincided with the recess 13 of an adjacent overlaying layer of the three-dimensional substrate 10 comprised in each spirally wound portion 111.

When the angle α is from 0.3 degrees to 60 degrees, the plurality of projections 12 and/or the plurality of recesses 13 of the three-dimensional substrate 10 may form a repetitive unit comprising a polygon such as an hexagon (n=60), an octagon (n=8), an enneagon (n=9), a decagon (n=10), a dodecagon (n=12) or an icosagon (n=20).

Figure 13:
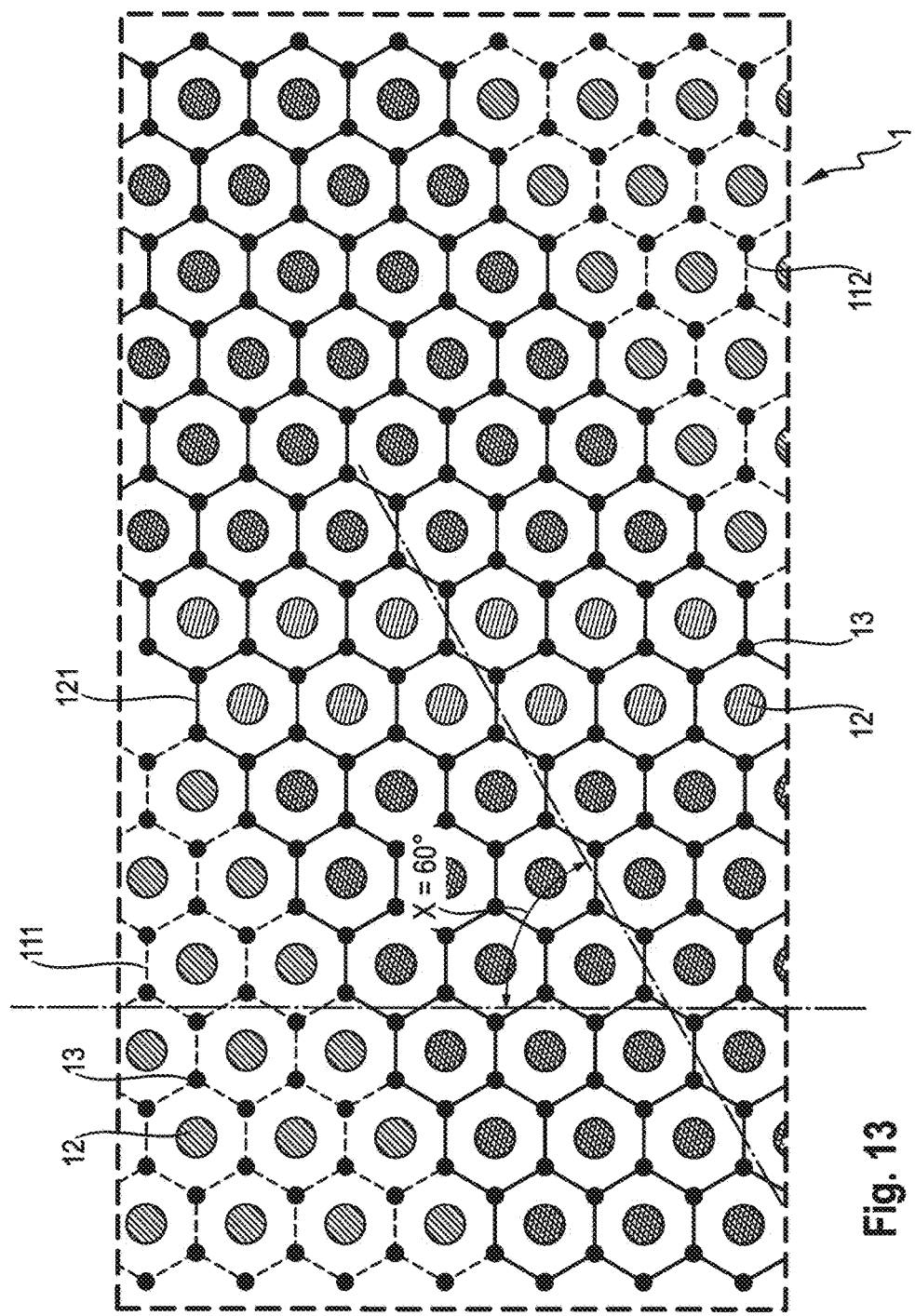
FIG. 13 is a front view of two spirally wound portions of a three-dimensional substrate being connected by a helically wound portion, with the three-dimensional substrate having a repetitive unit comprising a hexagon, having six sides, six corners and having a center, wherein either each recess of the plurality of the recesses is positioned at each corner of the hexagon while a projection of the plurality of the projections is respectively positioned at the center of the hexagon.

FIG. 13 is a front view of two spirally wound lanes of a three-dimensional substrate being connected by a helically wound, with the three-dimensional substrate having a repetitive unit comprising a hexagon, having six sides, six corners and having a center, wherein either each recess of the plurality of the recesses is positioned at each corner of the hexagon while a projection of the plurality of the projections is respectively positioned at the center of the hexagon.

In FIG. 13, each helically wound portion 121 may form an angle α=360/6=60 degrees relative to the transversal axis Tt of an adjacent spirally wound portion 111, 112 such that the projections 12 of the three-dimensional substrate 10 in each helically wound portion 121 may be at least partially nested with the projections 12 of an adjacent overlaying layer of the three-dimensional substrate 10 comprised in each spirally wound portion 111, 112 adjacent to the helically wound portion 121.

Method

A method 100 of winding the three-dimensional substrate 10 about the core 2 to form the spool 1 is provided. The three-dimensional substrate 10 has a plane P and comprising a plurality of projections 12 extending outwardly from the plane P of the three-dimensional substrate 10. The three-dimensional substrate 10 is made of the group consisting of a nonwoven web, a film and combinations thereof. The core 2 has a longitudinal axis Lc and a length along the longitudinal axis Lc. The core 2 comprises first and second transversal side edges 21, 22.

The method 100 comprises forming a first plurality of spirally wound portions 110 and a first plurality of helically wound portions 120 by positioning an end of the three-dimensional substrate 10 on the core 2. The three-dimensional substrate 10 is spirally wound around the core 2 to form each spirally wound portion 111, 112, 113, 114, 115 of the first plurality of spirally wound portions 110. The spirally wound portions 111, 112, 113, 114, 115 of the first plurality of spirally wound portions 110 are located next to each other along the longitudinal axis Lc of the core 2 between the first transversal side edge 21 of the core 2 and the second transversal side edge 22 of the core 2.

The three-dimensional substrate 10 is helically wound around the core 2 along the longitudinal axis Lc of the core 2 to form each helically wound portion 121, 122, 123, 124 of the first plurality of helically wound portions 120. Each helically wound portion 121, 122, 123, 124 of the first plurality of helically wound portions 120 extends between two adjacent spirally wound portions of the first plurality of spirally wound portions 110.

The three-dimensional substrate 10 in each spirally wound portion 111, 112, 113, 114, 115 of the first plurality of spirally wound portions 110 is repeatedly and spirally wound around the core 2 to form a plurality of layers overlaying each other.

In each spirally wound portion, a majority of the projections of the three-dimensional substrate 10 of each layer are at least partially nested with a majority of the projections of the three-dimensional substrate 10 of an adjacent overlaying layer of the spirally wound portion.

The method 100 of winding a three-dimensional substrate 10 may comprise forming a second plurality of spirally wound portions 210 and a second plurality of helically wound portions 220 by spirally winding the three-dimensional substrate 10 around the first plurality of spirally wound portions 110 to form each spirally wound portion 211, 212, 213, 214 of the second plurality of spirally wound portions 210. The spirally wound portions 211, 212, 213, 214 of the second plurality of spirally wound portions 210 may be located next to each other along the longitudinal axis Lc of the core 2 between the second transversal side edge 22 of the core 2 and the first transversal side edge 21 of the core 2.

The three-dimensional substrate 10 in each spirally wound portion 211, 212, 213, 214 of the second plurality of spirally wound portions 210 may be repeatedly and spirally wound around the core 2 along the longitudinal axis Lc of the core 2 in a direction opposite of the first plurality of spirally wound portions 110, i.e. from the second transversal side edge 22 of the core 2 to the first transversal side edge 21 of the core 2.

The method 100 of winding a three-dimensional substrate 10 may comprise helically winding the three-dimensional substrate 10 around the first plurality of spirally wound portions 110 to form each helically wound portion 221, 222, 223, 224 of the second plurality of the helically wound portions 220.

The first helically wound portion 224 of the second plurality of helically wound portions 220 extends between the last spirally wound portion 115 of the first plurality of spirally wound portions 110 and the first spirally wound portion 214 of the second plurality of spirally wound portions 220. The other helically wound portion 221, 222, 223 of the second plurality of helically wound portions 220 extends between two adjacent spirally wound portions of the second plurality of spirally wound portions 210.

The spool 1 may comprise a third plurality of spirally wound portions 310 and a third plurality of helically wound portions 320, as exemplary shown in FIG. 5. The third plurality of helically wound portions 320 may be formed in the same manner as the second plurality of helically wound portion 320 and may have the same orientation as the first plurality of helically wound portions 120.

According to the method 100, more than three pluralities of spirally wound portions and helically wound portions can be formed.

Test Methods

Condition all samples at about 23° C.±2° C. and about 50%±2% relative humidity for 2 hours prior to testing.

The MD tensile property is measured according to a method using the WSP 110.4 (09) Tensile Method, with a 50 mm sample width, 100 mm gauge length, and 100 mm/min rate of extension.

Dry Caliper Measurement Test Method at 0.1 kPa

The intent of this method is to provide a procedure to determine the dry caliper of the three-dimensional substrate 10 taken from the spool 1 under predefined pressure. The test can be executed with a conventional caliper micrometer, such as Type DM 2000 available from Wolf-Messtechnik GmbH, Am St. Niclas Schacht 13, Freiberg (Germany), having a circular sample foot of 50 mm diameter, having a weight for the foot of 20.0 g and no additional weights is needed to adjust the pressure to 0.1 kPa.

The Dry Caliper measurement of the three-dimensional substrate 10 is carried out on the three following square samples: of 10 cm×10 cm centered on a single layer of the three-dimensional substrate 10 taken from the spool 1 (see below) to obtain the caliper of the three-dimensional substrate 10.

Sample Preparation

1. Prior to testing bring the test samples to equilibrium for at least 2 hours at 23° Celsius (±2° C.) and 50% (±2%) relative humidity.

Prepare three samples for each replicate of 10 cm×10 cm centered on a single layer of the three-dimensional substrate 10 taken from the spool 1 as followed: A first replicate can be taken from the spool close to the core. A second replicate can be taken in a location close to the middle of the spool (i.e. between the core and the distal portion away of the core—the outer portion of the spool—). A third replicate can be taken in a location close to the outer portion of the spool, which is the distal portion away of the core.

2. Cut the material in a dimension greater than the anvil used to contact the sample.

Basic Protocol for Dry Caliper

2. Prepare the Micrometer with the designated anvil and weights.

3. Zero the thickness gauge as described by the manufacturer before analyzing each sample portion.

4. Before using the micrometer, make sure that the pressure foot and anvil surfaces are clean, that the calibration of the instrument has been done, and that the instrument is mounted on a solid level surface free from noticeable vibration.

5. The sample is positioned under the caliper gauge with the wearer surface toward the sample contact foot.

6. The sample contact foot is gently lowered into contact with the surface of the sample.

7. A total pressure of 0.1 kPa is applied.

8. The caliper reading is taken 2 seconds after the foot comes into contact with the sample. The Dry caliper is the average of three replicates and is reported in millimeters rounded to the nearest 0.01 mm.

Height Tests

Substrate projection heights and overall substrate heights are measured using a GFM MikroCAD Premium instrument commercially available from GFMesstechnik GmbH, Teltow/Berlin, Germany.

The GFM MikroCAD Premium instrument includes the following main components:
  a) a DLP projector with direct digital controlled micro-mirrors;
  b) a CCD camera with at least a 1600×1200 pixel resolution;
  c) projection optics adapted to a measuring area of at least 40 mm×30 mm;
  d) recording optics adapted to a measuring area of at least 40 mm×30 mm;
  e) a table tripod based on a small hard stone plate;
  f) a blue LED light source;
  g) a measuring, control, and evaluation computer running ODSCAD software (version 6.2); and
  h) calibration plates for lateral (x-y) and vertical (z) calibration available from the vendor.

The GFM MikroCAD Premium system measures the surface height of a sample using the digital micro-mirror pattern fringe projection technique. The result of the analysis is a map of surface height (z-directional or z-axis) versus displacement in the x-y plane. The system has a field of view of 40×30 mm with an x-y pixel resolution of approximately 63 microns and approximately 4 µm height resolution. All testing is performed in a conditioned room maintained at about 23±2° C. and about 50±2% relative humidity.

A steel frame (80 mm×70 mm square, 6 mm thick with an opening 60 mm×40 mm square) is used to mount the specimen.

First take the three-dimensional substrate form the spool and allow it to equilibrate at 23±1° C. and 50±2% relative humidity for 2 hours. To obtain a specimen, lay the three-dimensional substrate on a bench with the projections directed upward. Five replicates obtained from five three-dimensional substrate samples from the spool are prepared for analysis.

Calibrate the instrument according to manufacturer's specifications using the calibration plates for lateral (x-y axis) and vertical (z axis) available from the vendor.

Place the steel plate and specimen on the table beneath the camera, with the wearer-facing surface oriented toward the camera. Center the specimen within the camera field of view, so that only the specimen surface is visible in the image. Allow the specimen to lay flat with minimal wrinkles.

Collect a height image (z-direction) of the specimen by following the instrument manufacturer's recommended measurement procedures. Select the Technical Surface/Standard measurement program with the following operating parameters: Utilization of fast picture recording with a 3 frame delay. Dual phase shifts are used with 1) 16 pixel stripe width with a picture count of 12 and 2) 32 pixel stripe width with a picture count of 8. A full Graycode starting with pixel 2 and ending with pixel 512. After selection of the measurement program, continue to follow the instrument manufacturer's recommended procedures for focusing the measurement system and performing the brightness adjustment. Perform the 3D measurement then save the height image and camera image files.

Load the height image into the analysis portion of the software via the clipboard. The following filtering procedure is then performed on each image: 1) removal of invalid points; 2) removal of peaks (small localized elevations); 3) polynomial filtering of the material part with a rank of n=5, with exclusion of 30% of the peaks and 30% of the valleys from the material part, and 5 cycles.

Identify projections, recesses and plane on the substrate.

Figure 14:
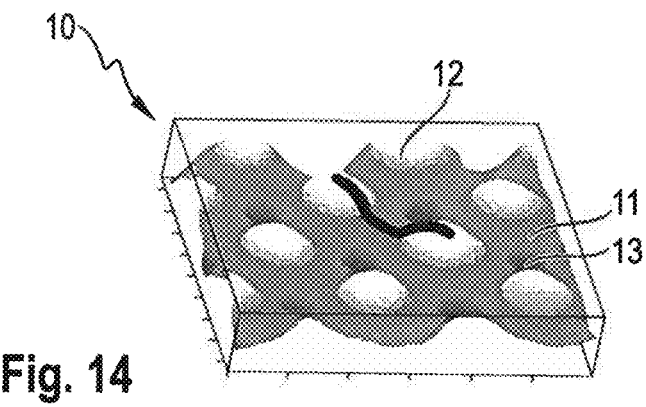
FIG. 14 is a top perspective view of a screenshot relating to a map of the surface height (z-axis) of a three-dimensional substrate versus displacement in a x-y plane.
Figure 15:
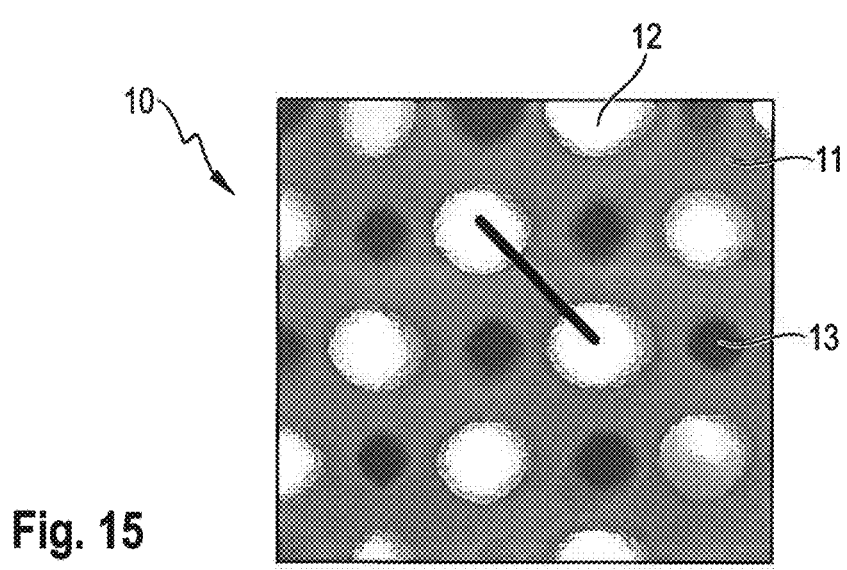
FIG. 15 is a top view of FIG. 14.
Figure 16:
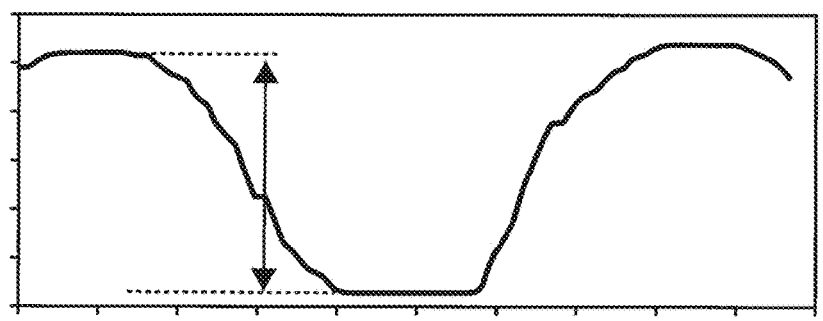
FIG. 16 is an height image corresponding to FIG. 14 which has been loaded into the analysis portion of the software used in the Height Tests.

Projection Height Test
  1. Draw a line connecting the top peaks of two adjacent projections, with the line crossing a land area located between them (See FIGS. 14 and 15);
  2. Generate a sectional image of the height image along the drawn line. Along the sectional line, measure the vertical height (z-direction) difference between the top peak of the projection and the adjacent valley of the land area. Record the height to the nearest 0.1 µm (See FIG. 16); and
  3. Repeat the measurement for 10 different projections. Average 10 height measures and report this value to the nearest 0.1 µm. This is the projection height.

Figure 17:
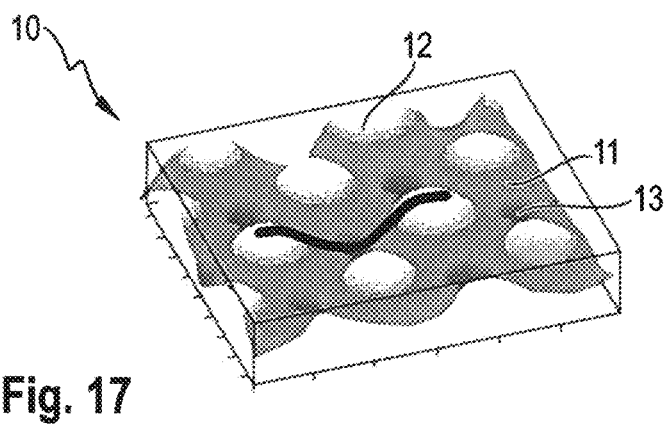
FIG. 17 is a top perspective view of a screenshot relating to a map of the surface height (z-axis) of a three-dimensional substrate versus displacement in a x-y plane.
Figure 18:
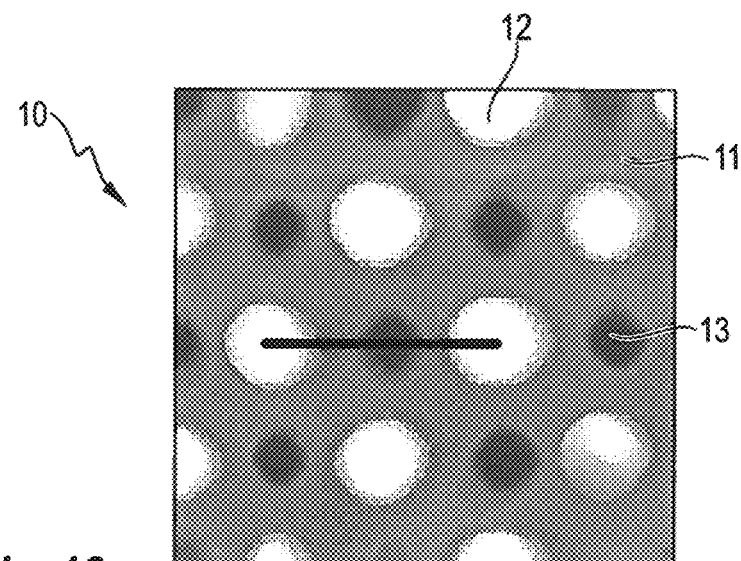
FIG. 18 is a top view of FIG. 17.
Figure 19:
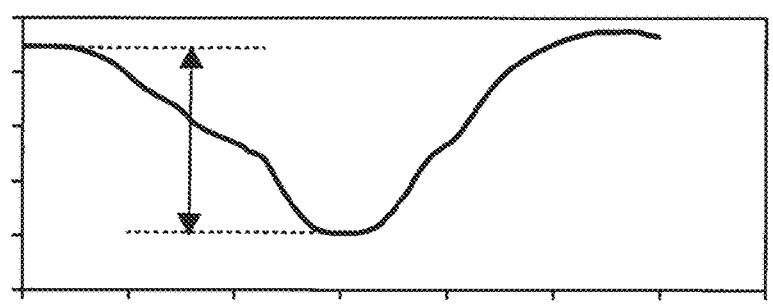
FIG. 19 is a height image corresponding to FIG. 17 which has been loaded into the analysis portion of the software used in the Height Tests.

Overall Substrate Height Test
1. Draw a line connecting the top peaks of two adjacent projections, with the line crossing the center of a recess located between each of the projections and within a recess (See FIGS. 17 and 18);
2. Generate a sectional image of the height image along the drawn line. Along the sectional line, measure the vertical height difference between the top peak of the projection and the adjacent base of the recess. Record the height to the nearest 0.1 μm (See FIG. 19); and
3. Repeat projection top peak to base of recess height measurements for 10 different projections. Average together 10 measurements and report this value to the nearest 0.1 μm. This is the overall substrate height.

Figure 20:
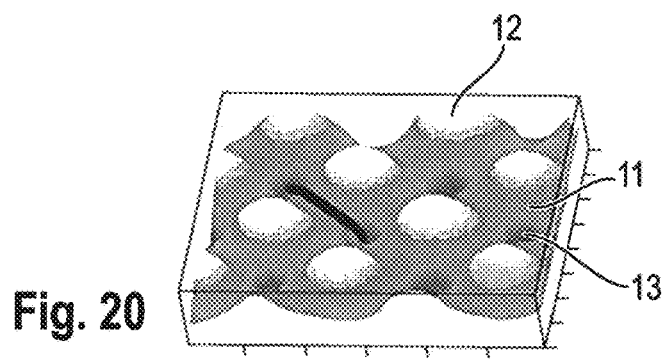
FIG. 20 is a top perspective view of a screenshot relating to a map of the surface height (z-axis) of a three-dimensional substrate versus displacement in a x-y plane.
Figure 21:
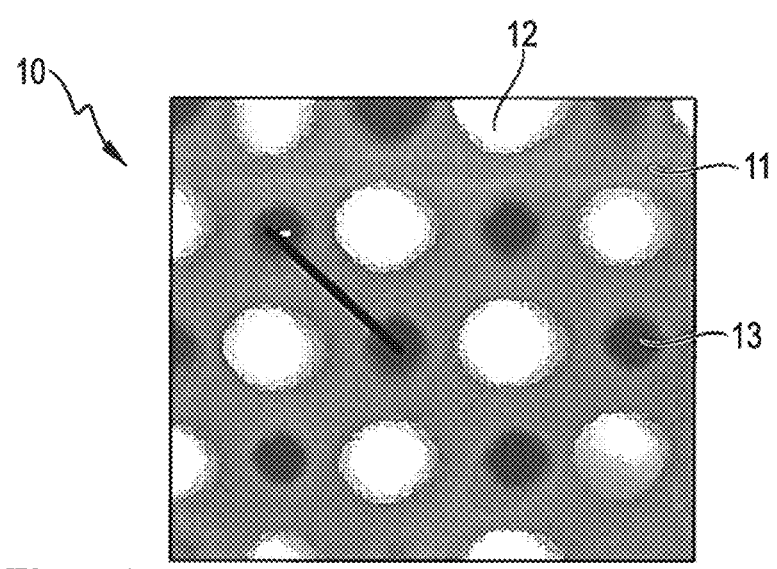
FIG. 21 is a top view of FIG. 20.
Figure 22:
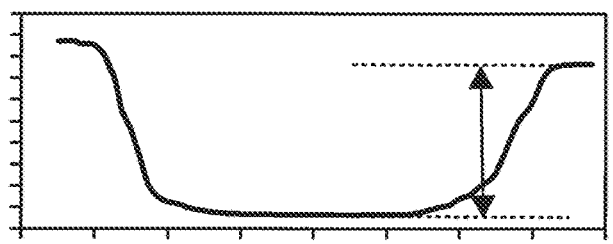
FIG. 22 is a height image corresponding to FIG. 20 which has been loaded into the analysis portion of the software used in the Height Tests.

Recess Height Test
1. Draw a line connecting the base of two adjacent recesses, with the line crossing a land area located between each of the recesses (See FIGS. 20 and 21);
2. Generate a sectional image of the height image along the drawn line. Along the sectional line, measure the vertical height (z-direction) difference between the base of the recess and the adjacent valley of the land area. Record the height to the nearest 0.1 μm (See FIG. 22).
3. Repeat measurement for 10 different recesses. Average 10 measurements and report this value to the nearest 0.1 μm. This is the projection height.

When the pattern configuration does not allow measuring one of the z-direction heights described above, it can be calculated from the equation: Overall Substrate Height=Projection Height+Recess Height.

In cases where the three-dimensional substrate only comprises a plurality of projections and recesses without any land areas or plane P, the above Dry Caliper measurement Test Method at 0.1 kPa shall be applied.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A spool comprising a three-dimensional substrate and a core,
the three-dimensional substrate having a plane and comprising a plurality of projections extending outwardly from the plane of the three-dimensional substrate;
wherein the three-dimensional substrate is made from the group consisting of a nonwoven web, a film and combinations thereof;
the core having a longitudinal axis and a length along the longitudinal axis;
the core comprising first and second transversal side edges;
wherein the spool comprises a first plurality of spirally wound portions and a first plurality of helically wound portions;
wherein the three-dimensional substrate is spirally wound around the core to form each spirally wound portion of the first plurality of spirally wound portions; and
wherein the spirally wound portions of the first plurality of spirally wound portions are located next to each other along the longitudinal axis of the core between the first transversal side edge of the core and the second transversal side edge of the core;
wherein the three-dimensional substrate is helically wound around the core along the longitudinal axis of the core to form each helically wound portion of the first plurality of helically wound portions; and
wherein each helically wound portion of the first plurality of helically wound portions extends between two adjacent spirally wound portions of the first plurality of spirally wound portions;
wherein the three-dimensional substrate in each spirally wound portion of the first plurality of spirally wound portions is repeatedly and spirally wound around the core to form a plurality of layers overlaying each other; and
wherein in each spirally wound portion, a majority of the projections of the three-dimensional substrate in at least some of the layers are at least partially nested with a majority of the projections of the three-dimensional substrate of an adjacent overlaying layer of the spirally wound portion; wherein the three-dimensional substrate comprises a longitudinal axis; wherein each projection comprises a base; wherein the base of each projection comprises a circumference where each projection starts to protrude outwardly from the plane; and wherein a notional circle is drawn around the base of each projection which is as small as possible without intersecting the circumference of the base of each projection; wherein each notional circle of each projection comprises a center; wherein two neighboring projections are aligned in a direction substantially parallel to a machine direction; wherein the distance between the centers of the notional circles of the respective neighboring projections has a length, L; wherein the diameter of the circle of one of the neighboring projections has a length, L1; wherein the minimum distance between the circumferences of the notional circles of the respective neighboring projections has a length, L2; such that the ratio of L1:L is at least 0.3 and the ratio of 0 L2:L 0.7.

2. The spool according to claim 1, wherein the spool only comprises the first plurality of spirally wound portions and the first plurality of helically wound portions, wherein each spirally wound portion has a diameter from 0.5 m to 2.0 m.

3. The spool according to claim 1, wherein the spool comprises a second plurality of spirally wound portions and a second plurality of helically wound portions;

wherein the three-dimensional substrate is spirally wound around the first plurality of spirally wound portions to form each spirally wound portion of the second plurality of spirally wound portions; and wherein the spirally wound portions of the second plurality of spirally wound portions are located next to each other along the longitudinal axis of the core between the second transversal side edge of the core and the first transversal side edge of the core;

wherein the three-dimensional substrate in each spirally wound portion of the second plurality of spirally wound portions is repeatedly and spirally wound around the core along the longitudinal axis of the core in a direction opposite of the first plurality of spirally wound portions;

wherein the three-dimensional substrate is helically wound around the first plurality of spirally wound portions to form each helically wound portion of the second plurality of helically wound portions;

wherein the first helically wound portion of the second plurality of helically wound portions extends between the last spirally wound portion of the first plurality of spirally wound portions and the first spirally wound portion of the second plurality of spirally wound portions; and the other helically wound portions of the second plurality of helically wound portions extend between two adjacent spirally wound portions of the second plurality of spirally wound portions.

4. The spool according to claim 3, wherein a majority of the projections of the three-dimensional substrate of a uppermost layer of a spirally wound portion of the first plurality of spirally wound portions are at least partially nested with a majority of the projections of the three-dimensional substrate of a lowermost layer of a directly above spirally wound portion of another plurality of spirally wound portions wound on the respective spirally wound portion of the first plurality of spirally wound portions.

5. The spool according to claim 3, wherein each spirally wound portions of each plurality of spirally wound portions positioned adjacent to the first or second transversal side edge of the core have higher number of layers than the other spirally wound portions of each plurality of spirally wound portions of the spool.

6. The spool according to claim 1, wherein each of the helically wound portions of the spool includes from 0.25 to 5 layers of the three-dimensional substrate wound around the core or the first plurality of spirally wound portions.

7. The spool according to claim 1, wherein the side edges of the layers of the plurality of layers of the three-dimensional substrate in each spirally wound portion are substantially aligned with each other.

8. The spool according to claim 1, wherein each plurality of spirally wound portions comprises from 3 to 30 spirally wound portions.

9. The spool according to claim 1, wherein the projections extending outwardly from the plane of the three-dimensional substrate represent from 30% to 70% of the total area of the three-dimensional substrate.

10. The spool according to claim 1, wherein the distance between the centers of the notional circles of the respective neighboring projections is from 2 mm to 15 mm.

11. The spool according to claim 1, wherein the length L1, is from 2 mm to 15 mm.

12. The spool according to claim 1, wherein the projections of the three-dimensional substrate have a z-directional height from 500 µm to 4000 µm according to the Projection Height Test.

13. The spool according to claim 1, wherein each spirally wound portion has a longitudinal axis substantially parallel to the longitudinal axis of the core and a transversal axis perpendicular to the longitudinal axis of the spirally wound portion, wherein each helically wound portion forms an angle from 0.3 degrees to 60 degrees relative to the transversal axis of an adjacent spirally wound portion.

14. The spool according to claim 13, wherein the three-dimensional substrate comprises a plurality of recesses, wherein each projection of the plurality of projections is next to at least one recess of the plurality of recesses, wherein the plurality of projections and the plurality of recesses of the three-dimensional substrate form a repetitive unit comprising a polygon having n sides, n corners and having a center, wherein either each recess of the plurality of the recesses or each projection of the plurality of the projections is positioned at each corner of the polygon while a projection of the plurality of the projections or a recess of the plurality of the recesses is respectively positioned at the center of the polygon;

wherein each helically wound portion forms an angle=360/n relative to the transversal axis of an adjacent spirally wound portion such that the projections of the three-dimensional substrate in each helically wound portion are at least partially nested with the projections of an adjacent overlaying layer of the three-dimensional substrate comprised in each spirally wound portion adjacent to the helically wound portion;

and wherein n≥6.

15. The spool according to claim 14, wherein the three-dimensional substrate comprises a plurality of land areas, wherein the land areas surround the plurality of projections and the plurality of the recesses, wherein a majority of the projections of the three-dimensional substrate of each layer of each spirally wound portion is nested with a majority of the projections of the three-dimensional substrate of an adjacent overlaying layer of the same spirally wound portion and/or of an adjacent spirally wound portion, wherein a majority of the recesses of the three-dimensional substrate of each layer are nested with a majority of the recesses of the three-dimensional substrate of an adjacent overlaying layer of the same spirally wound portion and/or of an adjacent spirally wound portion.

16. The spool according to claim 14, wherein the recesses of the plurality of the recesses have a z-directional height in the range of 200 µm to 2000 µm according to the Recess Height Test, and wherein the three-dimensional substrate has an overall z-directional height in the range of 700 µm to 6000 µm according to the Overall Substrate Height Test anywhere in the spool.

17. The spool according to claim 1, wherein the plurality of projections of the three-dimensional substrate form a repetitive pattern, wherein the repetitive pattern is characterized by a quasi-symmetry or a rotational symmetry according to an angle of less than 90 degrees such that the projections of the three-dimensional substrate in each helically wound portion are at least partially nested with the projections of an adjacent overlaying layer of the three-dimensional substrate comprised in each spirally wound portion adjacent to the helically wound portion.

18. A method of winding a three-dimensional substrate about a core to form a spool, the three-dimensional substrate having a plane and comprising a plurality of projections extending outwardly from the plane of the three-dimensional substrate;
wherein the three-dimensional substrate is made from the group consisting of a nonwoven web, a film and combinations thereof;
the core having a longitudinal axis and a length along the longitudinal axis;
the core comprising first and second transversal side edges;
the method comprising the following steps:
(a) forming a first plurality of spirally wound portions and a first plurality of helically wound portions by:
i) positioning an end of the three-dimensional substrate on the core;
spirally winding the three-dimensional substrate around the core to form each spirally wound portion of the first plurality of spirally wound portions; and wherein the spirally wound portions of the first plurality of spirally wound portions are located next to each other along the longitudinal axis of the core between the first transversal side edge of the core and the second transversal side edge of the core;
ii) helically winding the three-dimensional substrate around the core along the longitudinal axis of the core to form each helically wound portion of the first plurality of helically wound portions;
and wherein each helically wound portion of the first plurality of helically wound portions extends between two adjacent spirally wound portions of the first plurality of spirally wound portions;
wherein the three-dimensional substrate in each spirally wound portion of the first plurality of spirally wound portions is repeatedly and spirally wound around the core to form a plurality of layers overlaying each other; and
wherein in each spirally wound portion, a majority of the projections of the three-dimensional substrate of each layer are at least partially nested with a majority of the projections of the three-dimensional substrate of an adjacent overlaying layer of the spirally wound portion; wherein the three-dimensional substrate comprises a longitudinal axis; wherein each projection comprises a base; wherein the base of each projection comprises a circumference where each projection starts to protrude outwardly from the plane; and wherein a notional circle is drawn around the base of each projection which is as small as possible without intersecting the circumference of the base of each projection; wherein each notional circle of each projection comprises a center; wherein two neighboring projections are aligned in a direction substantially parallel to a machine direction; wherein the distance between the centers of the notional circles of the respective neighboring projections has a length, L; wherein the diameter of the circle of one of the neighboring projections has a length, $L1$; wherein the minimum distance between the circumferences of the notional circles of the respective neighboring projections has a length, $L2$; such that the ratio of $L1:L$ is at least 0.3 and the ratio of 0 $L2:L$ 0.7.

19. The method of winding a three-dimensional substrate according to claim 18, wherein the method comprises the following steps:
(b) forming a second plurality of spirally wound portions and a second plurality of helically wound portions by:
iii) spirally winding the three-dimensional substrate around the first plurality of spirally wound portions to form each spirally wound portion of the second plurality of spirally wound portions; and wherein the spirally wound portions of the second plurality of spirally wound portions are located next to each other along the longitudinal axis of the core between the second transversal side edge of the core and the first transversal side edge of the core;
wherein the three-dimensional substrate in each spirally wound portion of the second plurality of spirally wound portions is repeatedly and spirally wound around the core along the longitudinal axis of the core in a direction opposite of the first plurality of spirally wound portions;
iv) helically winding the three-dimensional substrate around the first plurality of spirally wound portions to form each helically wound portion of the second plurality of the helically wound portions; and
wherein the first helically wound portion of the second plurality of helically wound portions extends between the last spirally wound portion of the first plurality of spirally wound portions and the first spirally wound portion of the second plurality of spirally wound portions; and
wherein the other helically wound portion of the second plurality of helically wound portions extends between two adjacent spirally wound portions of the second plurality of spirally wound portions.

* * * * *